(12) United States Patent
Hsu et al.

(10) Patent No.: US 8,024,125 B2
(45) Date of Patent: *Sep. 20, 2011

(54) METHODS AND APPARATUS TO MONITOR CONTAMINATION LEVELS IN A FORMATION FLUID

(75) Inventors: Kai Hsu, Sugar Land, TX (US); Peter S. Hegeman, Stafford, TX (US); Chengli Dong, Sugar Land, TX (US); Ricardo Vasques, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 141 days.

This patent is subject to a terminal disclaimer.

(21) Appl. No.: 12/362,602

(22) Filed: Jan. 30, 2009

(65) Prior Publication Data

US 2009/0150079 A1 Jun. 11, 2009

Related U.S. Application Data

(63) Continuation of application No. 11/764,284, filed on Jun. 18, 2007, now Pat. No. 7,711,488.

(60) Provisional application No. 60/882,285, filed on Dec. 28, 2006.

(51) Int. Cl.
*G01V 8/00* (2006.01)
*E21B 49/08* (2006.01)
(52) U.S. Cl. ........................ 702/11; 73/152.42
(58) Field of Classification Search .................... 702/11; 73/61.52, 61.48, 61.44, 152.42
See application file for complete search history.

(56) References Cited

U.S. PATENT DOCUMENTS

| | | | |
|---|---|---|---|
| 4,994,671 A | 2/1991 | Safinya et al. |
| 5,235,285 A | 8/1993 | Clark et al. |
| 5,266,800 A | 11/1993 | Mullins |
| 6,107,796 A | 8/2000 | Prammer |
| 6,134,952 A | 10/2000 | Garver et al. |
| 6,234,030 B1 | 5/2001 | Butler |
| 6,274,865 B1 | 8/2001 | Schroer et al. |

(Continued)

FOREIGN PATENT DOCUMENTS

WO 02057596 7/2002

(Continued)

OTHER PUBLICATIONS

Mullins, O. et al., Real-Time Quantification of OBM Filtrate Contamination During Openhole Wireline Sampling by Optical Spectroscopy, SPWLA 41st Annual Meeting, Dallas, Texas, Jun. 2000.

(Continued)

*Primary Examiner* — John Fitzgerald
(74) *Attorney, Agent, or Firm* — David J Smith

(57) ABSTRACT

Apparatus and methods to monitor contamination levels in a formation fluid are disclosed. An example method involves obtaining first property data indicative of a first fluid property of a formation fluid and second property data indicative of a second fluid property of the formation fluid. A correlation between the first and second property data is generated and third data is fitted to the correlation. A fitting parameter is determined based on the third data indicative of an amount of change of the first property data relative to an amount of change of the second property data.

20 Claims, 17 Drawing Sheets

U.S. PATENT DOCUMENTS

| | | |
|---|---|---|
| 6,343,507 B1 | 2/2002 | Felling et al. |
| 6,350,986 B1 | 2/2002 | Mullins et al. |
| 6,476,384 B1 | 11/2002 | Mullins et al. |
| 6,714,872 B2 | 3/2004 | DiFoggio et al. |
| 6,748,328 B2 | 6/2004 | Storm, Jr. et al. |
| 6,799,117 B1 | 9/2004 | Proett et al. |
| 6,956,204 B2 | 10/2005 | Dong et al. |
| 7,299,136 B2 | 11/2007 | DiFoggio et al. |
| 7,398,159 B2 | 7/2008 | Venkataramanan et al. |
| 2004/0254732 A1 | 12/2004 | Storm, Jr. et al. |
| 2005/0182566 A1 | 8/2005 | DiFoggio |
| 2005/0216196 A1 | 9/2005 | Akkurt et al. |
| 2006/0000603 A1 | 1/2006 | Zazovsky et al. |
| 2006/0155472 A1 | 7/2006 | Venkataramanan et al. |
| 2006/0155474 A1 | 7/2006 | Venkataramanan et al. |
| 2006/0236758 A1 | 10/2006 | DiFoggio |
| 2006/0241866 A1 | 10/2006 | DiFoggio |
| 2006/0250130 A1 | 11/2006 | Akkurt et al. |
| 2007/0119244 A1 | 5/2007 | Goodwin et al. |
| 2008/0083273 A1 | 4/2008 | Sroka et al. |

FOREIGN PATENT DOCUMENTS

| | | |
|---|---|---|
| WO | 02057597 | 7/2002 |

OTHER PUBLICATIONS

Mulllins, O. et al., Real-Time Determination of Filtrate Contamination During Openhole Wireline Sampling by Optical Spectroscopy, Dallas, Texas, Oct. 2000, SPE63071.

Mullins, O. et al., Linearity of Near-Infrared Spectra of Alkanes, Applied Spectroscopy, vol. 54, No. 4, 2000.

Dong, C. et al., Advances in Downhole Contamination Monitoring and GOR Measurement of Formation Fluid Samples, SPWLA 44th Annual Logging Symposium, Jun. 2003.

McCullaugh, P. et al., Generalized Linear Model, 2nd Edition, Chapman and Hall, 1989.

Walpole, R., Probability and Statistics for Engineers and Scientists, 7th Edition, Prentice Hall, 2002.

Hammond, P., One- and Two-Phase Flow During Fluid Sampling by a Wireline Tool, Kluwer Academic Publishers, 1991.

Box, G. et al., Time Series Analysis: Forecasting and Control, Third Edition, Prentice Hall, 1994.

Meyer, R. et al, Natural Bitumen and Extra Heavy Oil, Ch. 4, 2004, Survey of Energy Resources, p. 93-117.

Heron, J. et al., Ann. Rev. Energy, 1983, 8, 137-163.

Oblad, A. et al., Ann. Rev. Energy, 1987, 12, 283-356.

Speight, J., Ann. Rev. Energy 1986, 11, 253-274.

Ovalles, C. et al., Fuel, 1995, 74, 1162-1168.

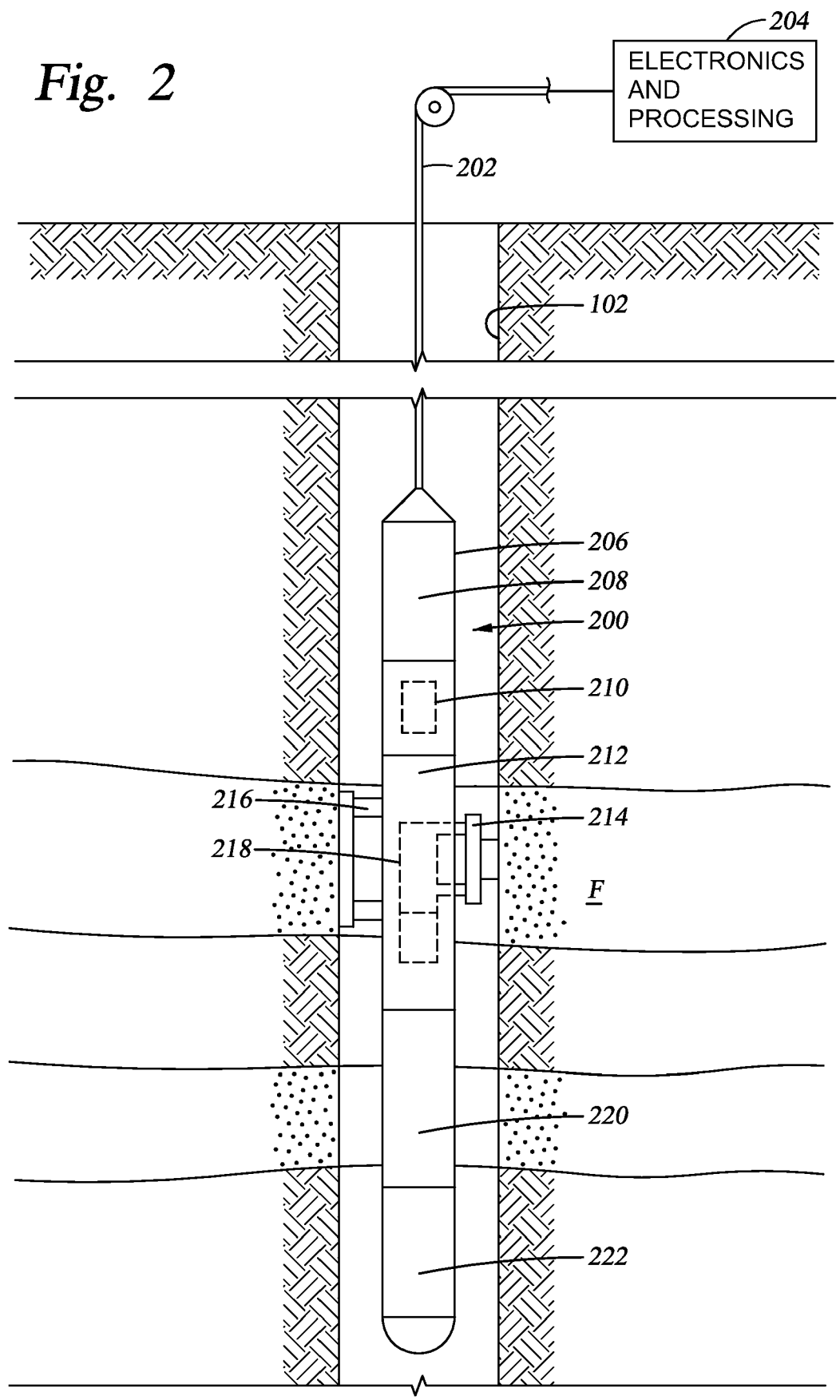

US 8,024,125 B2

METHODS AND APPARATUS TO MONITOR CONTAMINATION LEVELS IN A FORMATION FLUID

RELATED APPLICATIONS

This application is a continuation of U.S. patent application Ser. No. 11/764,284, filed on Jun. 18, 2007, and now issued as U.S. Pat. No. 7,711,488, which claims the benefit of U.S. Provisional Application 60/882,285, filed on Dec. 28, 2006.

FIELD OF THE DISCLOSURE

The present disclosure relates generally to measuring formation fluids and, more particularly, to methods and apparatus to monitor contamination levels in a formation fluid.

BACKGROUND

Drilling, completion, and production of reservoir wells involve measuring various subsurface formation parameters. Companies often measure percentages of oil, water, and gas mixtures contained in representative fluid samples drawn from wells to determine formation fluid quality. The formation fluid quality of a particular well can be used to determine the economic value of extracting fluid from the reservoir well. Generating accurate measurements of formation fluid requires drawing fluid samples substantially free of contaminants from a reservoir well to avoid generating measurements reflective of contaminants introduced into the reservoir well.

Contaminants are often introduced into a well during a drilling process. For example, to facilitate a drilling process, a drilling mud is introduced into the well as a lubricant to reduce the effects of friction between a drill bit and a formation wall of the well. Contamination of formation fluid occurs when the filtrate of the drilling mud permeates the formation wall during and after drilling. When drawing formation fluid samples to measure formation fluid quality, the formation fluid samples often contain a mixture of formation fluid and mud filtrate. The amount of mud filtrate in a formation fluid sample indicates the contamination level (i.e., the amount of contamination) of the formation fluid sample. If the filtrate is miscible with the formation fluid (e.g., when a well penetrating a hydrocarbon-bearing formation is drilled with oil base mud (OBM)), the filtrate contamination in the formation fluid can reduce the quality of formation fluid samples and make subsequent pressure, volume, and temperature (PVT) analysis unreliable or even incorrect.

To obtain a sample containing formation fluid substantially free of contaminants, a fluid extractor (e.g., a pump) in a downhole drillstring or a downhole wireline tool is used to extract or pump fluid from the formation until the extracted fluid is substantially free of contaminants. Known techniques for determining when a sample is substantially free of contaminants involve measuring optical density (OD) (i.e., optical absorbance) of fluid samples using a single channel (i.e., corresponding to a single wavelength) of a spectrometer. For a mixture of formation fluid and mud filtrate, a measured optical density at a particular wavelength ($\lambda$) is linearly related to a contamination level. As the contamination levels of drawn samples decrease as pumping time increases, the measured optical density values change to indicate the changing contamination levels. Using these known techniques to measure contamination levels involves using equations and several assumed parameter values determined empirically over time using measured data from various reservoir wells. However, the empirical nature of such parameter values often leads to inefficiencies in well testing. For example, using such parameter values to determine the amount of time to pump in one well before obtaining a formation fluid sample substantially free of contaminants may result in pumping for a relatively longer duration than necessary in that well. On the other hand, using the same parameter values to determine a pumping time for another well may lead to pumping for an insufficient duration, which causes acquiring erroneous measurements of extracted formation fluid samples having relatively high contamination levels.

SUMMARY

In accordance with a disclosed example, an example method to measure fluid properties involves obtaining first property data indicative of a first fluid property of a formation fluid and second property data indicative of a second fluid property of the formation fluid. A correlation between the first and second property data is then generated. Third data is fitted to the correlation. A fitting parameter is determined based on the third data indicative of an amount of change of the first property data relative to an amount of change of the second property data.

In accordance with another disclosed example, an example apparatus includes a data interface configured to obtain first property data indicative of a first fluid property of a formation fluid and second property data indicative of a second fluid property of the formation fluid. The example apparatus also includes a data relationship processor configured to generate a correlation between the first and second property data. The example apparatus also includes a data fitter configured to fit third data to the correlation. The data relationship processor is configured to determine a fitting parameter based on the third data indicative of an amount of change of the first property data relative to an amount of change of the second property data.

In accordance with another disclosed example, an example method involves obtaining optical density measurement data of a fluid, determining a logarithmic derivative data of the optical density measurement data, and determining a linear relationship between the logarithmic derivative data and fluid pumpout volume data. A rate of change value is determined based on the linear relationship. The rate of change value is representative of an amount of change in the logarithmic derivative data relative to an amount of change in the fluid pumpout volume data. A contamination level in the fluid is determined based on the rate of change value.

In accordance with another disclosed example, an example apparatus to measure fluid contamination includes a data interface configured to obtain optical density measurement data of a fluid and a data fitter configured to determine logarithmic derivative data of the optical density measurement data. The example apparatus also includes a data relationship processor configured to determine a rate of change value based on a linear relationship between the logarithmic derivative data and fluid pumpout volume data. The rate of change value is representative of an amount of change in the logarithmic derivative data relative to an amount of change in the fluid pumpout volume data. The example apparatus also includes a contamination value generator configured to determine a contamination level in the fluid based on the rate of change value.

BRIEF DESCRIPTION OF THE DRAWINGS

FIG. 2 depicts an example wireline tool for testing a formation and analyzing the composition of fluids from the formation as described herein.

DETAILED DESCRIPTION

Figure 1:
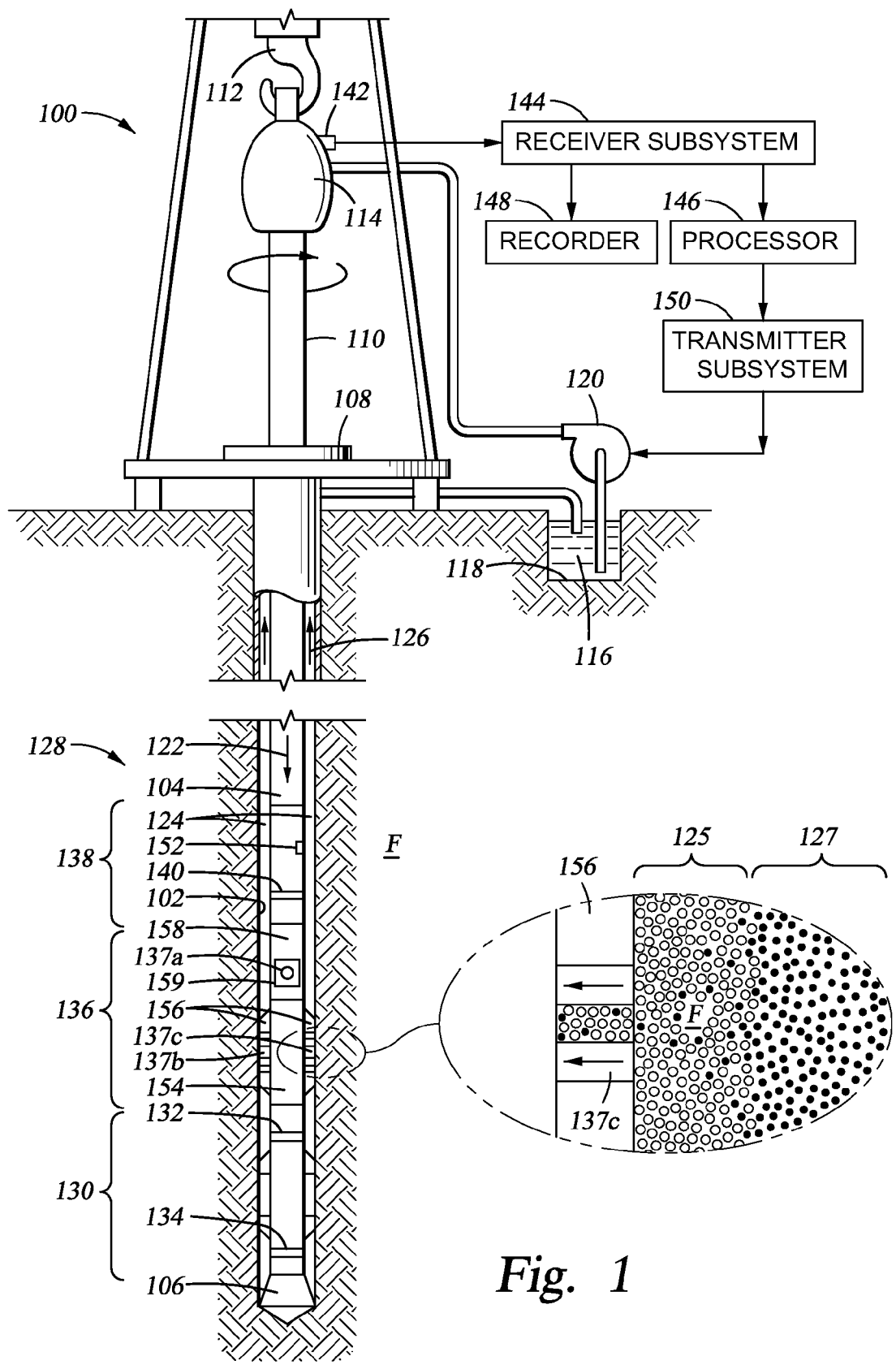
FIG. 1 is an elevational view including a block diagram of a drilling rig and drill string that may be used to implement the example methods and apparatus described herein.

Certain examples are shown in the above-identified figures and described in detail below. In describing these examples, like or identical reference numbers are used to identify common or similar elements. The figures are not necessarily to scale and certain features and certain views of the figures may be shown exaggerated in scale or in schematic for clarity and/or conciseness.

The example methods and apparatus described herein can be used to monitor contamination levels in fluid samples extracted from a formation to, for example, obtain a formation fluid sample having a relatively lower amount of contamination (e.g., mud filtrate contaminant from a drilling mud) than a formation fluid sample obtained during an initial fluid extraction phase. In addition, the example methods and apparatus described herein can be used to relatively accurately determine an amount of contamination in a formation fluid sample. In this manner, a formation fluid sample having a relatively low contamination level and/or a known amount of contamination can be used to measure the properties of formation oil in a reservoir well. Unlike known methods used to determine a contamination level of a formation fluid sample by measuring an optical density of the fluid sample using a single channel (or a single wavelength) (e.g., a color channel or a methane channel) of a spectrometer, the example methods and apparatus described herein are configured to measure optical densities of a fluid sample using a plurality of channels (i.e., a plurality of wavelengths) of a spectrometer to determine a contamination level in the fluid sample. Although the example methods and apparatus are described below as using a plurality of wavelengths, in other example implementations, the example methods and apparatus may use fewer wavelengths or one wavelength in combination with density measurement or concentration measurement (e.g., $H_2S$ concentration, etc.), two or more nuclear magnetic resonance (NMR) measurements (e.g., relaxation time and diffusivity), fluorescence at two wavelengths, reflection index at two wavelengths, resistivity, capacitance, etc.

Furthermore, even though the present disclosure described or assumes that the various fluid measurements are obtained from a single sensor at a single location, it should be understood that multiple sensors can be distributed along a flowline or fluid conduit, in which case it may be desirable to place the sensors in close proximity of each other. Alternatively, if the sensors are placed sufficiently apart, delay correction method may be implemented to ensure that the sensors are measuring the same fluid. For example, one or more flowrate measurements may be made to properly time the measurements of the sensors.

The wavelengths of the various channels used to monitor contamination as described herein can range from visible wavelength light to mid-infrared wavelength light, including near-infrared light, and each wavelength can have a different sensitivity to contaminants (e.g., mud filtrate from drilling mud that invades a formation). Although each wavelength has a different sensitivity to contaminants, the optical density or optical absorbance measured using each wavelength channel nonetheless contains some valuable information about the contamination level in a fluid sample. By substantially simultaneously measuring a formation fluid sample using a plurality of wavelength channels, the optical density data contains some contaminant level information that is redundant among the different wavelength channel data. In contrast, using a known single-channel measurement method to measure a formation fluid sample using a color channel, for example, can produce contamination level data that vary from contamination level data determined using another known single-channel measurement method that uses a methane channel, for example. The variance between the channels may be caused by differing levels of noise between the single-channel measurements and/or the different sensitivities of the wavelengths. This variance between the single-channel measurements, regardless for the reason, will reduces the confidence one has in those measurements.

The example methods and apparatus described herein use the redundant information in each of the wavelength channel data to determine the contamination levels in fluid samples extracted from a formation. In particular, the redundant information in each channel facilitates correlating or fitting the measurement data from the different channels to determine a contamination level that is consistent with the data in all of the channels. Thus, the example methods and apparatus described herein can be used to obtain relatively more accurate contamination level values than contamination level values obtained using known single-channel methods. The example methods and apparatus described herein can also be used to determine a quality control (QC) value (i.e., a confidence value) indicative of statistical variations of the contamination levels caused by noise in OD data.

The Beer Lambert law defines a linear relationship between optical absorbance (i.e., optical density) and concentrations of substances or materials in measured fluid samples. Accordingly, the Beer Lambert law can be used as a basis to determine the buildup of formation oil concentrations relative to contamination materials in fluid samples. For a fluid sample containing a mixture of formation oil and mud filtrate, the measured optical density (OD) of the fluid sample at a wavelength ($\lambda$) (i.e., $OD_\lambda$) is linearly related to the contamination ($\eta$) in the fluid sample according to equation 1 below.

$$OD_\lambda = \eta \cdot OD_{\lambda,fil} + (1-\eta) \cdot OD_{\lambda,oil} \qquad \text{Equation 1}$$

In equation 1 above, the optical density of a mud filtrate (e.g., a contaminant) ($OD_{\lambda,fil}$) at the wavelength $\lambda$ is multiplied by the contamination $\eta$ to produce a product $\eta \cdot OD_{\lambda,fil}$, and the optical density of formation oil ($OD_{\lambda,oil}$) at the wavelength $\lambda$ is multiplied by a value of the contamination $\eta$ subtracted from one to produce a product $(1-\eta) \cdot OD_{\lambda,oil}$. The measured optical density of a fluid sample $OD_\lambda$ is then the sum of the products $\eta \cdot OD_{\lambda,fil}$ and $(1-\eta) \cdot OD_{\lambda,oil}$. Assuming that the contamination $\eta$ changes with respect to a pumping time during which fluid is extracted from a formation, the values of the optical densities $OD_\lambda$ of the extracted fluid samples will reflect the contamination levels in the fluid samples. Of course, if $OD_{\lambda,fil} = OD_{\lambda,oil}$, the sensitivity to contamination materials diminishes. However, there are many wavelengths where the optical densities of formation oil and contamination material such as mud filtrate differ significantly and facilitate determining contamination levels in fluid samples and, thus, determining the build up of concentrations of formation oil relative to the contamination levels in the fluid samples as fluid is extracted from a formation over time. In alternative example implementations, mixing laws other than or in addition to the Beer Lambert law can be used to determine the buildup of formation oil concentration levels. For example, mixing laws defining linear relationships can be used in connection with density measurements and mixing laws defining non-linear relationships can be used in connection with electromagnetic measurements (e.g., NMR measurements).

To determine a contamination level in a fluid sample, equation 1 above can be rearranged algebraically as shown in equation 2 below.

$$\eta = \frac{OD_{\lambda,oil} - OD_\lambda}{OD_{\lambda,oil} - OD_{\lambda,fil}} \qquad \text{Equation 2}$$

As shown in equation 2 above, the optical density of a fluid sample $OD_\lambda$ is subtracted from the optical density of formation oil $OD_{\lambda,oil}$ to produce a value $OD_{\lambda,oil} - OD_\lambda$, and optical density of mud filtrate $OD_{\lambda,fil}$ is subtracted from the optical density of formation oil $OD_{\lambda,oil}$ to produce a value $OD_{\lambda,oil} - OD_{\lambda,fil}$. The contamination $\eta$ is then determined by dividing the value $OD_{\lambda,oil} - OD_\lambda$ by the value $OD_{\lambda,oil} - OD_{\lambda,fil}$. If the optical density of mud filtrate $OD_{\lambda,fil}$ and the optical density of formation oil $OD_{\lambda,oil}$ are known, equation 2 above can be used to determine the concentration of filtrate or amount of contamination $\eta$ (i.e., a contamination level) in a fluid sample using the measured optical density $OD_\lambda$ of the fluid sample. The example methods and apparatus described below can be used to determine the values of the optical density of mud filtrate $OD_{\lambda,fil}$ and the optical density of formation oil $OD_{\lambda,oil}$ to determine the concentration of a contaminant $\eta$ and the concentration of formation oil in fluid samples based on optical densities $OD_\lambda$ of fluid samples measured using a plurality of wavelength channels of a spectrometer. In this manner, a buildup of formation oil concentrations in extracted fluid can be observed based on the measured optical densities $OD_\lambda$ of a plurality of fluid samples extracted from a formation over an extended duration.

To determine the optical density of mud filtrate $OD_{\lambda,fil}$ and the optical density of formation oil $OD_{\lambda,oil}$, the example methods and apparatus described herein are configured to determine a buildup exponent value ($\alpha$). The buildup exponent value $\alpha$ defines a rate of change indicative of an amount of change in the optical densities $OD_\lambda$ of measured fluid samples relative to the amount (i.e., volume) of fluid that has been extracted from a formation. The buildup exponent value $\alpha$ is related to the optical density OD of the extracted fluid as shown in equation 3 below.

$$OD(v) = C - \frac{D}{v^\alpha} \qquad \text{Equation 3}$$

As shown in equation 3 above, a cumulative pumping volume (v) indicative of an amount of fluid extracted from formation over time is raised to an exponential power of the buildup exponent value $\alpha$ to generate a volume-based formation oil concentration buildup model ($v^\alpha$). A parameter value (D) is then divided by the volume-based buildup model $v^\alpha$ to determine a quotient value $$\frac{D}{v^\alpha}.$$

The quotient value $$\frac{D}{v^\alpha}$$

is then subtracted from the asymptotic optical density value (C) (or a true optical density of the formation oil) (i.e., $OD_{oil}$) to determine the optical density OD(v) of the extracted formation fluid as a function of extracted fluid volume v. The asymptotic value (C) and parameter value (D) are fitting parameters. In the illustrated examples described herein, the asymptotic value (C) is used as the estimate of true optical density. The example methods and apparatus described herein use equation 3 above to determine the buildup exponent value α and, in turn, determine the contamination level of mud filtrate in fluid samples using the buildup exponent value α. In other example implementations, equations other than equation 3 above such as, for example, exponential based equations (e.g., $OD(v)=C-D\cdot\exp(-\alpha\cdot v)$) can be used to determine the buildup exponent value α. In the exponential equation $OD(v)=C-D\cdot\exp(-\alpha\cdot v)$, when the cumulative pumping volume (v) is zero, the optical density OD(v) is equal to the parameter value (D) subtracted from the asymptotic value (C) and as the cumulative pumping volume (v) reaches infinity, the optical density OD(v) is equal to the asymptotic value (C).

The example methods and apparatus described herein can be implemented in connection with a drilling process using a drill string having a drill bit to form a borehole in a formation and a tool collar having instrumentation (e.g., a spectrometer) to perform downhole measurements. An example derrick assembly 100 having an example drill string 104 is described in connection with FIG. 1. The example methods and apparatus described herein can also be implemented in connection with a borehole tool that is lowered into a borehole after a drillstring has been removed from the borehole (e.g., wireline) and that includes instrumentation (e.g., a spectrometer) to perform downhole measurements. An example borehole tool 200 is described below in connection with FIG. 2. In some example implementations, a tool collar of the drill string 104 and/or the borehole tool 200 can be configured to analyze the measurement data as described herein downhole, and in other example implementations, the tool collar may be configured to communicate the measurement data to a processor system at a surface location (e.g., a drilling platform) that analyzes the measurement data as described herein. It will be appreciated that the current disclosure is not limited to any one conveyance type, such as a drillpipe for example, but is equally applicable to coiled tubing, wireline, wired-drill-pipe, and other conveyance means known in the industry.

FIG. 1 shows a drilling system and related environment. Land-based platform and derrick assembly 100 are positioned over a wellbore 102 penetrating a subsurface formation F. The wellbore 102 (i.e., a borehole) is formed by rotary drilling in a manner that is well known. However, those of ordinary skill in the art, given the benefit of this disclosure, will appreciate that the methods and apparatus described herein also find application in directional drilling applications as well as rotary drilling, and is not limited to land-based rigs. The drill string 104 is suspended within the wellbore 102 and includes a drill bit 106 at its lower end. The drill string 104 is rotated by a rotary table 108, energized by means not shown, which engages a kelly 110 at the upper end of the drill string 104. The drill string 104 is suspended from a hook 112, attached to a traveling block (not shown), through the kelly 110 and a rotary swivel 114, which permits rotation of the drill string 104 relative to the hook 112.

A drilling fluid 116 is stored in a pit 118 formed at the well site. A pump 120 delivers the drilling fluid 116 to the interior of the drill string 104 via a port in the rotary swivel 114, inducing the drilling fluid 116 to flow downwardly through the interior of the drill string 104 as indicated by directional arrow 122. The drilling fluid 116 exits the drill string 104 via ports in the drill bit 106 to lubricate the drill bit 106 and then circulates upwardly through the region between an outer surface of the drill string 104 and the wall of the wellbore 102, called the annulus 124, as indicated by direction arrows 126. When the drilling fluid 116 enters and flows through the annulus 124, the drilling fluid 116 is mixed with formation cuttings and other formation material to form a drilling mud. The drilling mud carries formation cuttings up to the surface as the drilling mud is routed to the pit 118 for recirculation and so that the formation cuttings and other formation material can settle in the pit 118. The formation cuttings and/or other solids mixed with the drilling fluid 116 create a "mud-cake" that also performs various functions, such as coating the borehole wall.

In addition to lubricating the drill bit 116, the dense drilling fluid 116 conveyed by the pump 120 is used to maintain the drilling mud in the annulus 124 of the wellbore 102 at a pressure (i.e., an annulus pressure ("$A_P$")) that is typically higher than the pressure of fluid in the surrounding formation F (i.e., a pore pressure ("$P_P$")) to prevent formation fluid from passing from the surrounding formation F into the borehole. In other words, the annulus pressure ($A_P$) is maintained at a higher pressure than the pore pressure ($P_P$) so that the wellbore 102 is "overbalanced" ($A_P > P_P$) and does not cause a blowout. The annulus pressure ($A_P$) is also usually maintained below a given level to prevent the formation surrounding the wellbore 102 from cracking and to prevent the drilling fluid 116 from entering the surrounding formation F. Thus, downhole pressures are typically maintained within a given range.

Keeping the annulus pressure $A_P$ relatively higher than the pore pressure $P_P$ causes mud filtrate 125 from the drilling mud to enter or permeate the surrounding formation F, and consequently, fluid samples subsequently extracted from the formation F are typically contaminated with the mud filtrate 125. As shown in detail in FIG. 1, the mud filtrate 125 has permeated the formation F and mixed with formation oil 127 (e.g., formation fluid) that is to be measured to determine the economic value of extracting the formation oil via the wellbore 102. However, at a particular depth into the formation F, the formation F has oil 127 that is substantially free of contamination from the mud filtrate 125. When fluid is initially drawn from the formation F, the fluid will include a mix of the mud filtrate 125 and the oil 127. Using measurements of fluid samples contaminated with the mud filtrate 125 to determine a quality of the formation F generates inaccurate results that are not indicative of the true characteristics of the pure formation fluid of the formation F. However, because the mud filtrate 125 penetrates a finite distance into the formation F, fluid samples containing relatively less contamination material (e.g., the mud filtrate 125) than samples obtained during an initial pumping phase can be extracted from the formation F by pumping and extracting fluid from the formation F for an extended time. The example methods and apparatus described herein can be used to determine the contamination levels (i.e., the amount of the mud filtrate 125) in extracted fluid samples to determine when extracted fluid samples contain contamination levels below a particular threshold to enable measuring the samples to obtain data that is not substantially affected by contaminants. The acceptable contamination level threshold may vary between different applications depending on the desired quality level for a particular formation or the types of characteristics that are to be analyzed for a particular formation.

Although in some cases formation fluid without the mud filtrate 125 may include substances other than oil such as, for example, water, for purposes of discussion, the formation fluid will be referred to as formation oil or oil. In addition, although the analysis of contamination is discussed herein as an amount of drilling fluid that contaminates formation fluid, the example methods and apparatus can be used to analyze other types of contaminants. For example, a contaminant may be a drilling mud mixture created when drilling fluid mixes with formation fluid released from formation rock crushed by a drill bit (e.g., the drill bit 106 of FIG. 1) during a drilling or coring operation. In this manner, the example methods and apparatus can be used to analyze the variation of concentration of formation fluid and changes in the composition of formation fluid.

The drill string 104 further includes a bottom hole assembly 128 near the drill bit 106 (e.g., within several drill collar lengths from the drill bit 106). The bottom hole assembly 128 includes capabilities for measuring, processing, and storing information, as well as communicating with surface equipment. The bottom hole assembly 128 includes, among other things, measuring and local communications apparatus 130 for determining and communicating measurement information associated with the formation F surrounding the wellbore 102. The communications apparatus 130 includes a transmitting antenna 132 and a receiving antenna 134. A communication apparatus that may be used to implement the example communication apparatus 130 is described in detail in U.S. Pat. No. 5,339,037, commonly assigned to the assignee of the present application, the entire contents of which are incorporated herein by reference.

The bottom hole assembly 128 further includes a formation tester 136 that may comprise one or more drill collars such as drill collars 154 and 158. The formation tester 136 includes one or more probe(s) 137a-c, one or more of which can be configured to extract fluid samples from the formation F and perform measurement operations. The probe 137a may be located on a raised portion 159 (e.g., a pad) of an outside diameter of the formation tester 136. Alternatively, the probes 137b and 137c may be located in a stabilizer blade 156 of the formation tester 136. Alternatively or additionally, probes may be anywhere on the formation tester 136.

The bottom hole assembly 128 further includes a surface/local communications subassembly 138. As known in the art, the surface/local communications subassembly 138 may comprise a downhole generator (not shown) commonly referred to as a "mud turbine" that is powered by the drilling fluid 116 flowing downwardly through the interior of the drill string 104 in a direction generally indicated by arrow 122. The downhole generator can be used to provide power to various components in the bottom hole assembly 128 during circulation of the drilling fluid 116, for immediate use or for recharging batteries located in the bottom hole assembly 128.

The communications subassembly 138 further includes an antenna 140 used for local communication with the apparatus 130, and also includes a known type of acoustic communication system (not shown) that communicates with a similar system (not shown) at the Earth's surface via signals carried in the drilling fluid 116 or drilling mud. Thus, the surface communication system in the subassembly 138 includes an acoustic transmitter that generates an acoustic signal in the drilling fluid 116 or drilling mud that includes information of measured downhole parameters.

One suitable type of acoustic transmitter employs a device known as a "mud siren" (not shown). A mud siren includes a slotted stator and a slotted rotor that rotates and repeatedly interrupts the flow of the drilling fluid 116 or drilling mud to establish a desired acoustic wave signal in the drilling fluid 116. The driving electronics in the subassembly 138 may include a suitable modulator, such as a phase shift keying (PSK) modulator, which conventionally produces driving signals for the mud siren. For example, the driving signals can be used to apply appropriate modulation to the mud siren.

The acoustic signals transmitted by the acoustic communication system are received at the surface by transducers 142. The transducers 142 (e.g., piezoelectric transducers) convert the received acoustic signals to electronic signals. The outputs of the transducers 142 are coupled to an uphole receiving subsystem 144, which demodulates the transmitted signals. An output of the receiving subsystem 144 is then coupled to a processor 146 and a recorder 148. In the illustrated example, the recorder 148 includes a memory (not shown), and the recorder 148 is configured to store data received from the subassembly 138 in the memory.

An uphole transmitting system 150 is also provided, and is operative to control interruption of the operation of the pump 120 in a manner that is detectable by transducers 152 in the subassembly 138. In this manner, the subassembly 138 and the uphole equipment can communicate via two-way communications as described in greater detail in U.S. Pat. No. 5,235,285, the entire contents of which are incorporated herein by reference.

The order in which the local communications apparatus 130, the formation tester 136, and the surface/local communications subassembly 138, are depicted on the bottom hole assembly 128 in FIG. 1 is only one example implementation. In other example implementations, the components 130, 136, and 138, of the bottom hole assembly 128 may be rearranged or one or more components may be removed or added. In addition, the bottom hole assembly 128 may include fewer or more of any one or more of the components 130, 136, 138, and/or any other components not shown. The example methods and apparatus described herein are not restricted to drilling operations. Persons of ordinary skill in the art will appreciate that the example apparatus and methods described herein can also be advantageously used during, for example, well testing or servicing. Further, the example methods and apparatus, in general, can be implemented in connection with testing conducted in wells penetrating subterranean formations and in connection with applications associated with formation evaluation tools conveyed downhole by any known means.

FIG. 2 depicts the example borehole tool 200 for testing the formation F and analyzing the composition of fluids from the formation F as described herein. In the illustrated example, the tool 200 is a wireline tool, which is suspended in the wellbore 102 from the lower end of a multiconductor cable 202 that is spooled on a winch (not shown) at the Earth's surface. On the surface, the cable 202 is communicatively coupled to an electrical control system 204, which may include and be similar to the receiver subsystem 144, the processor, 146, the recorder 148, and the transmitter subsystem 150 described above in connection with FIG. 1. The tool 200 includes an elongated body 206 that includes a module 208 having a downhole portion of a tool control system 210 configured to control extraction of fluid from the formation F and measurements performed on the extracted fluid.

The elongated body 206 also includes a formation tester 212 having a selectively extendable fluid admitting assembly 214 and a selectively extendable tool anchoring member 216 that are respectively arranged on opposite sides of the body 206. The fluid admitting assembly 214 is configured to selectively seal off or isolate selected portions of the wall of wellbore 102 so that pressure or fluid communication with the adjacent formation F is established to draw fluid samples from the formation F. The formation tester 212 also includes a fluid analysis module 218 through which the obtained fluid samples flow. The fluid may thereafter be expelled through a port (not shown) or it may be sent to one or more fluid collecting chambers 220 and 222, which may receive and retain the fluids obtained from the formation F for subsequent testing at the surface or a testing facility. In the illustrated example, the electrical control system 204 and the downhole control system 210 are configured to control the fluid admitting assembly 214 to draw fluid samples from the formation F and to control the fluid analysis module 218 to measure the fluid samples. In some example implementations, the fluid analysis module 218 may be configured to analyze the measurement data of the fluid samples as described herein. In other example implementations, the fluid analysis module 218 may be configured to generate and store the measurement data and subsequently communicate the measured data to the surface for subsequent analysis of the measurement data at the surface. Although the downhole control system 210 is shown as being implemented separate from the formation tester 212, in some example implementations, the downhole control system 210 may be implemented in the formation tester 212.

Figure 3A:
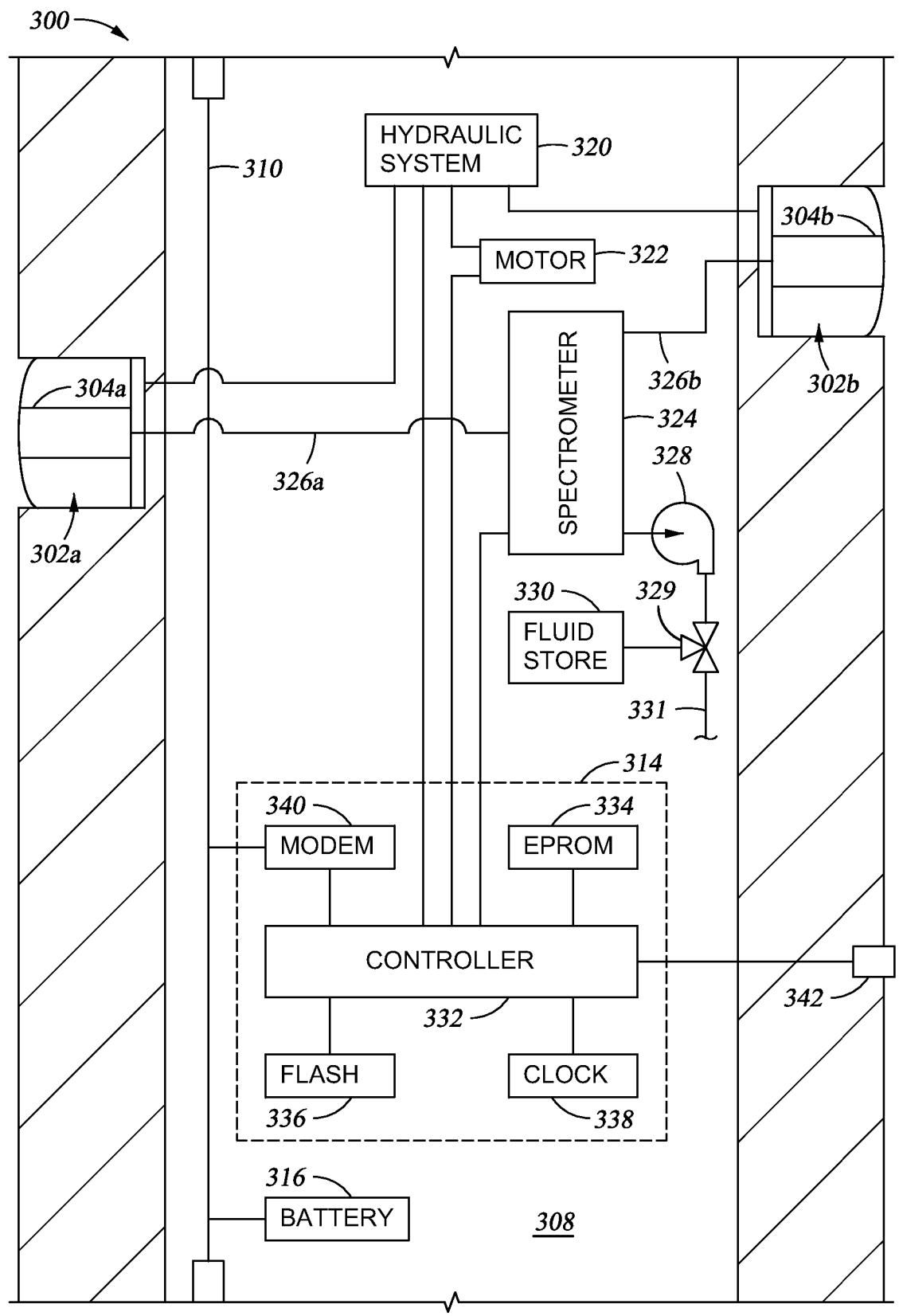
FIGS. 3A and 3B depict block diagrams of example formation testers that may be used to implement the example formation testers of FIGS. 1 and 2.
Figure 3B:
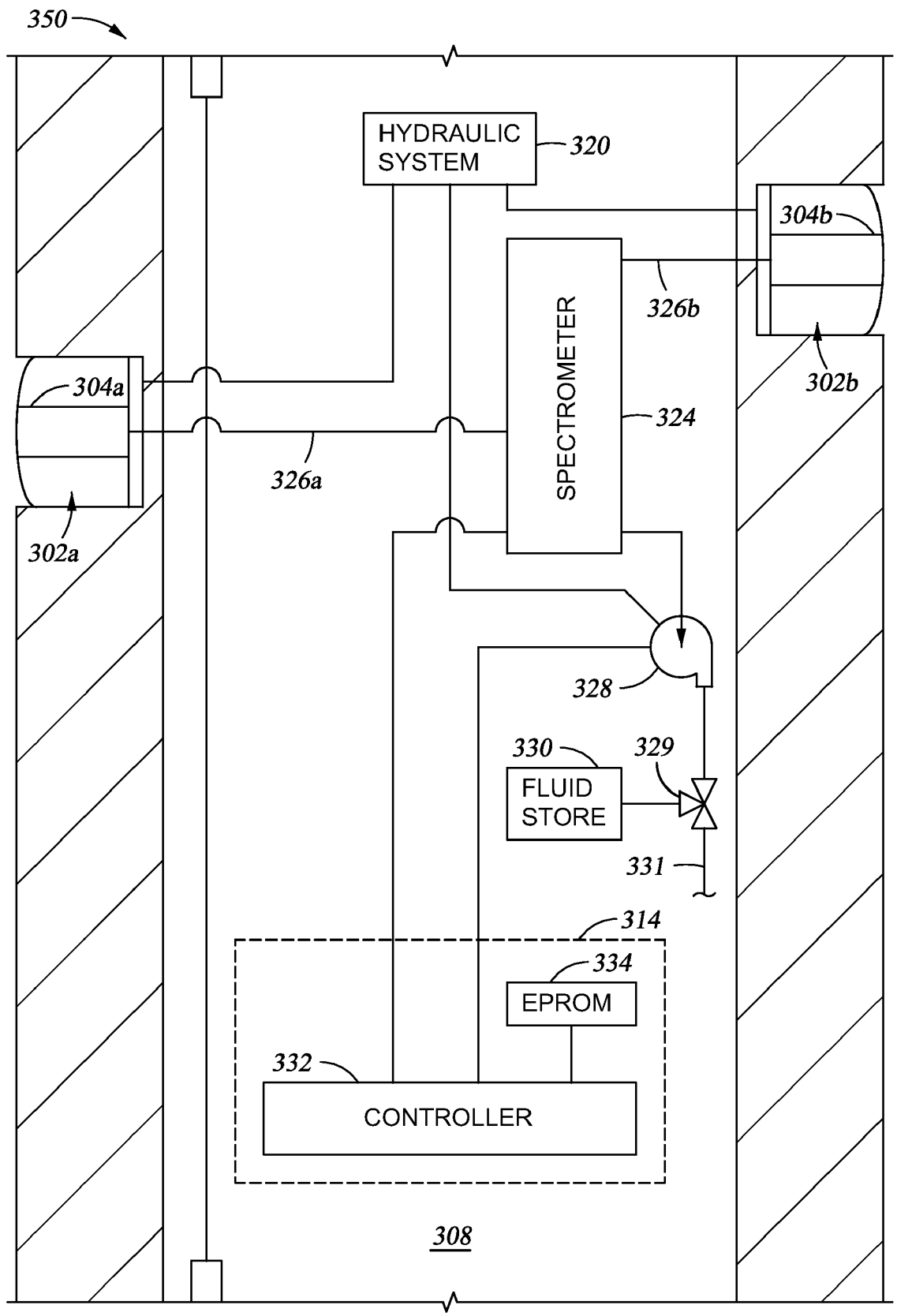

FIG. 3A depicts a block diagram of an example formation tester 300 that may be used to implement, for example, the formation tester 136 of FIG. 1 and configured to be used in a logging while drilling (LWD) application. FIG. 3B depicts a block diagram of a fluid extraction tool 350 that may be used to implement the tool 200 as described in FIG. 2 to extract and store fluid samples that can be brought to the surface for subsequent analysis. In the illustrated examples of FIGS. 3A and 3B, lines shown connecting blocks represent fluid, electrical, and/or mechanical connections that may comprise one or more flow lines (e.g., hydraulic fluid flow lines or formation fluid flow lines) or one or more wires or conductive paths respectively. For the sake of clarity and brevity some of the lines operatively connecting part of the tools or modules, be they fluid or electrical connections, have not been shown.

Turning in detail to FIG. 3A, to perform downhole measurements and tests, the formation tester 300 is provided with probes 302*a* and 302*b*. In an example implementation, respective ports 304*a-b* are formed in each of the probes 302*a-b* to admit formation fluid into the formation tester 300. In alternative example implementations, inflatable packers can be used instead of the probes 302*a-b* to establish fluid connections with formations and draw fluid samples.

To provide electronic components and hydraulic components to control the probes 302*a-b* and obtain test and measurement values, the formation tester 300 is provided with a chassis 308 that includes a tool bus 310 configured to transmit electrical power and communication signals. The chassis 308 also includes an electronics system 314 and a battery 316 electrically coupled to the tool bus 310. The chassis 308 further includes a hydraulic system 320 and an optional motor 322. The hydraulic system 320 and/or the motor 322 may be configured to power a pump 328 for extracting formation fluid via the ports 304*a-b* of the probes 302*a-b*.

The chassis 308 is provided with a spectrometer 324 to measure the optical density (OD) of formation fluid samples. For example, the spectrometer 324 may include one or more optical sources configured to provide photons having energies corresponding to different wavelengths and a plurality of optical detectors for determining the intensity of the light sources at the various wavelengths as well as the intensity of the light transmitted through the fluid samples at those wavelengths. The optical detectors can be positioned so that they measure the same portion of fluid substantially simultaneously. Alternatively, the optical detectors can be staggered at known distances and delays determined based on the known distances and the flow rate of fluid through the spectrometer 324 can be used to associate OD measurements generated by the various optical detectors that correspond to the same portion of fluid. A spectrometer that may be used to implement the example spectrometer 324 to measure the optical densities of formation fluid samples at a plurality of energy channels or a plurality of wavelengths is described in U.S. Pat. No. 4,994,671 issued to Safinya et al. In the illustrated example, fluid from the formation F flows through the ports 304*a-b* to the spectrometer 324 via flow paths 326*a* and 326*b*. In other example implementations in which measurements (e.g., density measurements, NMR measurements, resistivity measurements, capacitance measurements, etc.) other than or in addition to OD measurements are used, the spectrometer 324 may be replaced or supplemented with other types of suitable sensors including, for example, NMR sensors, density sensors, resistivity sensors, capacitance sensors, etc.

The spectrometer 324 is in line with the pump 328 via fluid passageways. The pump 328 is configured to draw formation fluid through the inlet ports 304*a-b* of the probes 302*a-b* and through the spectrometer 324 to enable the spectrometer 324 to measure the extracted formation fluid. When the controller 332 determines that contamination levels in the measured formation fluid are below a particular contamination level threshold, a valve 329 routes the fluid samples to a fluid store 330. The fluid store 330 may be implemented using a one or more tanks or bottles. When contamination levels of fluid samples are not below the threshold value, the fluid samples are routed into the wellbore and/or out of the formation tester 300 via passageway 331.

The electronics system 314 is provided with a controller 332 (e.g., a CPU and Random Access Memory) to implement test and measurement routines (e.g., to control the spectrometer 324, etc.). To store machine accessible instructions that, when executed by the controller 332, cause the controller 332 to implement test and measurement processes or any other processes, the electronics system 314 is provided with an electronic programmable read only memory (EPROM) 334. In the illustrated example, the controller 332 is configured to receive digital data from various sensors in the formation tester 300. The controller 332 is also configured to execute different instructions depending on the data received. The instructions executed by the controller 332 may be used to control some of the operations of the formation tester 300. Thus, the formation tester 300 is preferably, but not necessarily, configured to sequence some of its operations (e.g., formation fluid sample measurements) according to contamination levels in formation fluid measured in situ.

To store, analyze, process and/or compress test and measurement data, or any kind of data, acquired by the formation tester 300 using, for example, the spectrometer 324, the electronics system 314 is provided with a flash memory 336. To generate timestamp information corresponding to the acquired test and measurement information, the electronics system 314 is provided with a clock 338. The timestamp information can be used during a playback phase to determine the time at which each measurement was acquired. For some measurement data, the timestamps may be used to determine the depth at which the formation tester 300 was located within a wellbore (e.g., the wellbore 102 of FIG. 1) when the measurements were acquired. To communicate information when the formation tester 300 is downhole, the electronics system 314 is provided with a modem 340 that is communicatively coupled to the tool bus 310 and the subassembly 138 (FIG. 1). In the illustrated example, the formation tester 300 is also provided with a read-out port 342 to enable retrieving measurement information stored in the flash memory 336 when the testing tool is brought to surface. The read-out probe 342 may be an electrical contact interface or a wireless interface that may be used to communicatively couple a data collection device to the formation tester 300 to retrieve logged measurement information stored in the flash memory 336. Additionally, the formation tester 300 may send and/or receive data from the surface via the subassembly 138 (FIG. 1) and the modem 340.

Turning in detail to FIG. 3B, the fluid extraction tool 350 is configured to measure optical densities of extracted fluid samples, and when contamination levels in fluid samples are below a particular threshold, the fluid extraction tool 350 is configured to store the fluid samples to be brought to the surface for subsequent analyses. For purposes of discussion, like components of the fluid extraction tool 350 and the formation tester 300 of FIG. 3A are assigned the same reference numerals.

As shown in FIG. 3B, the fluid extraction tool 350 is provided with the pump 328. The pump 328 is configured to draw formation fluid through the ports 304a-b of the probes 302a-b and through the spectrometer 324. The spectrometer 324 measures the extracted formation fluid to determine optical density values. When the controller 332 determines that contamination levels in the measured fluid samples are below a particular contamination level threshold, the valve 329 routes the fluid samples to the fluid store 330. The fluid store 330 may be implemented using one or more tanks or bottles. When contamination levels of fluid samples are not below the threshold value, the fluid samples are routed out of the fluid extraction tool 350 via the passageway 331.

Although the components of FIGS. 3A and 3B are shown and described above as being communicatively coupled and arranged in a particular configuration, persons of ordinary skill in the art will appreciate that the components of the formation tester 300 and/or the fluid extraction tool 350 can be communicatively coupled and/or arranged different from what is shown in FIGS. 3A and 3B without departing from the scope of the present disclosure. In some example implementations, the example methods and apparatus can be used in connection with a guarded probe system. In a guarded probe system, the example methods and apparatus may be used to measure and analyze fluid drawn in a sample flow line, a guarded flow line, or a combination thereof.

Figure 4:
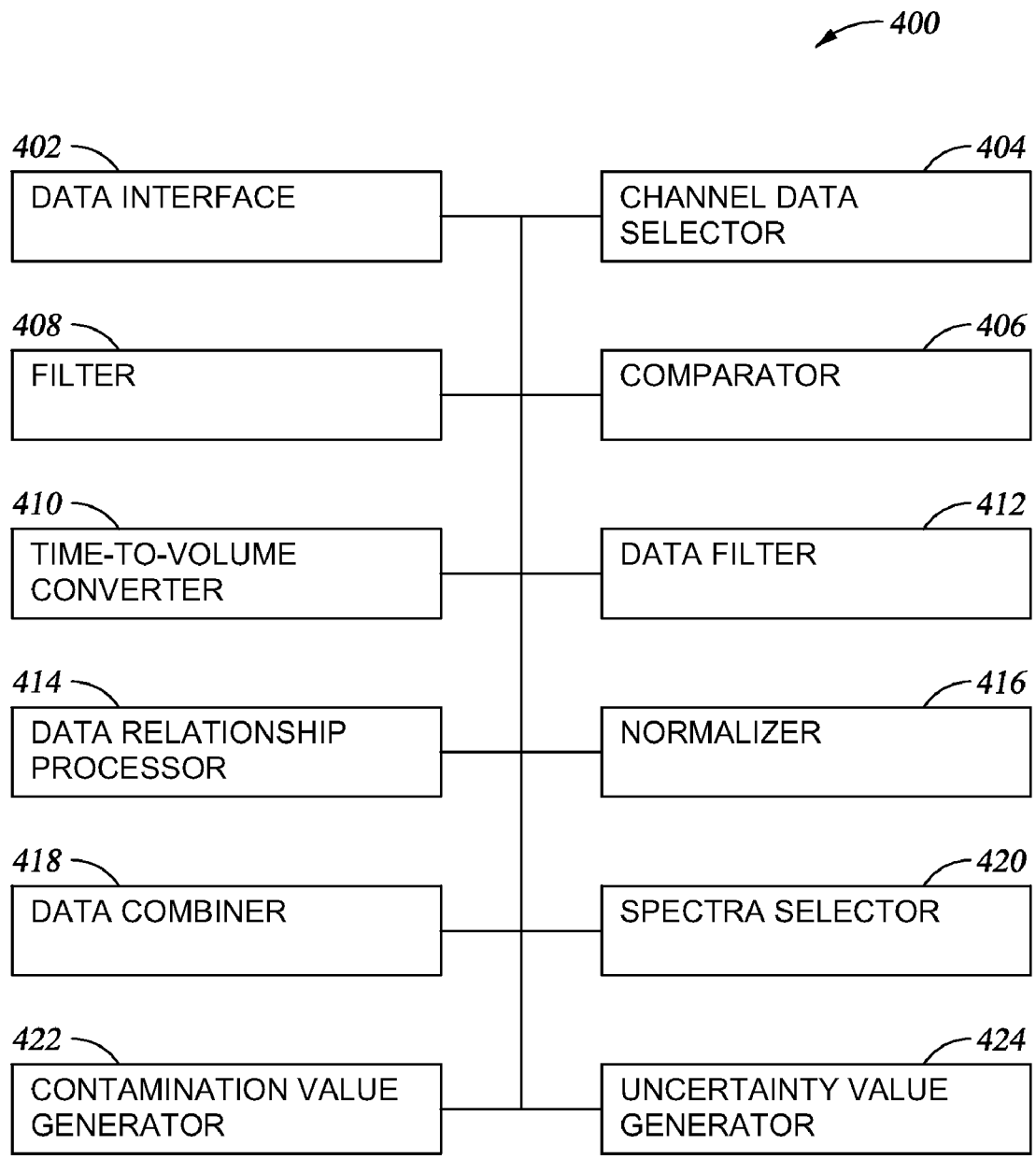
FIG. 4 depicts a block diagram of an example apparatus that may be used to determine the contamination levels of fluid samples extracted from a formation.

FIG. 4 depicts a block diagram of an example apparatus 400 that may be used to determine the contamination levels of fluid samples extracted from the formation F (FIGS. 1 and 2). The example apparatus 400 may be implemented using any desired combination of hardware, firmware, and/or software. For example, one or more integrated circuits, discrete semiconductor components, or passive electronic components may be used. Additionally or alternatively, some or all of the blocks of the example apparatus 400, or parts thereof, may be implemented using instructions, code, and/or other software and/or firmware, etc. stored on a machine accessible medium that, when executed by, for example, a processor system (e.g., the example electronics system 314 of FIG. 3A), perform the operations represented in the flowchart of FIGS. 5 and 6. Although the example apparatus 400 is described as having one of each block described below, the example apparatus 400 may be provided with two or more of any block described below. In addition, some blocks may be disabled, omitted, or combined with other blocks.

To obtain optical data measurement values from a storage file, the example apparatus 400 is provided with a data interface 402. For example, if the controller 332 (FIG. 3A) stores OD measurement values from the spectrometer 324 or any other types of measurement values (e.g., NMR values, density values, resistivity values, capacitance values, etc.) in a log file in the flash memory 336, the data interface 402 may be configured to retrieve the measurement values from the flash memory 336. Alternatively, if the processor 146 (FIG. 1) at a surface station stores the optical data measurement values in the recorder 148 (FIG. 1), the data interface 402 may be configured to retrieve the measurement values from the recorder 148. In the illustrated example, the data interface 402 is also configured to retrieve other types of data and to store any type of data in a memory or memories. If the example apparatus is configured to analyze fluid samples in real time, the data interface 402 can be configured to retrieve and store data associated with the real-time analysis.

To select OD data that is suitable for analyzing contamination levels, the apparatus 400 is provided with a channel data selector 404. During a measurement acquisition phase, the spectrometer 324 (FIG. 3A) measures the OD of fluid extracted from the formation F using a plurality of wavelength channels as described in greater detail below. Some of the OD channel data may not be suitable for use in analyzing contamination levels. In some cases, OD data acquired using particular wavelength channels may not be suitable for determining contamination levels because the selected wavelength was not sufficiently sensitive to the contamination material. The channel data selector 404 may be configured to select useable OD data based on whether the OD data is within particular threshold levels (e.g., greater than a minimum threshold value or less than a maximum threshold value). When types of measurements (e.g., NMR measurements, density measurements, resistivity measurements, capacitance measurements, etc.) other than optical density are used, the channel data selector 404 may be configured to select useable data of the other measurement types based on comparisons to threshold levels. For example, if a plurality of NMR channels are used, the NMR channels comprising T1 and/or T2 relaxation spectrum amplitudes corresponding to a plurality of relaxation times, the channel data selector 404 may select data corresponding to relaxation times having amplitude levels sufficiently sensitive to contamination.

To perform comparisons between OD data or between OD data and other values (e.g., threshold values) or between data other than OD data, the example apparatus 400 is provided with a comparator 406. For example, the channel data selector 404 may be configured to use the comparator 406 to compare predetermined threshold values with OD data from different channels to determine which channel data is useable for analyzing contamination levels.

To filter OD data, the example apparatus is provided with a filter 408. In the illustrated example, the filter 408 is configured to filter out noise, inconsistent data, erroneous data, or other information from OD data values measured using the spectrometer 324 (FIG. 3A). For example, the filter 408 can be configured to remove particular OD data values based on filter criteria. In addition, the filter 408 can be configured to perform averaging of OD data or subtraction of OD data or values from other OD data to generate filtered OD data.

To convert time-based measurement OD data to volume-based measurement OD data, the example apparatus 400 is provided with a time-to-volume converter 410. In some example implementations, the controller 332 is configured to store time-based OD measurement data during a data acquisition phase in which the spectrometer 324 (FIG. 3A) measures OD's of fluid samples. To facilitate analyzing the OD measurement data when the formation tester 300 does not pump or extract fluid from the formation F at a constant rate, the time-to-volume converter 410 can be configured to covert the time-based OD measurement data (i.e., OD(t)) to volume-based OD measurement data (i.e., OD(v)). To facilitate converting time-based data to volume-based data, the controller 332 stores data indicative of fluid extraction rate or pumping rate variations relative to time in a log file while the formation tester 300 extracts fluid from the formation F. The time-to-volume converter 410 is configured to convert the time-based data to volume-based data using the pumping rate variation data.

To fit data to line plots, line functions, or to other data, the example apparatus 400 is provided with a data fitter 412. As described in greater detail below, determining contamination levels in fluid samples entails fitting OD measurement data to other data such as, for example, curve plots, line functions, straight-line data, or other OD measurement data to find a linear relationship between the fitted data. The data fitter 412 can also be configured to fit data to non-linear functions.

In addition, to determine linear and/or non-linear relationships between data such as, for example, between OD measurement data acquired using a channel and OD measurement data acquired using another channel, the example apparatus 400 is provided with a data relationship processor 414. In the illustrated example, the data relationship processor 414 is configured to determine rate of change values (i.e., slopes) and intercept values associated with linear and/or non-linear relationships between data.

To normalize data, the example apparatus 400 is provided with a normalizer 416. For example, the normalizer 416 can be used to normalize OD measurement data acquired using a particular channel to OD measurement data acquired using another channel. Also, the normalizer 416 can be used to normalize OD measurement data acquired using a plurality of channels to OD measurement data designated as reference data.

To combine data such as, for example, OD measurement data acquired using one channel with OD measurement data acquired using another channel, the example apparatus is provided with a data combiner 418. As described in greater detail below, OD measurement data acquired using different wavelength channels can be combined to substantially reduce the amount of noise acquired by each wavelength channel. That is, the measurement data that is redundant from channel to channel is data that reflects substantially accurate OD's of fluid samples. Whereas sporadic data that is not redundant from channel to channel reflects the noise in the channels. By combining the OD measurement data from different channels, the redundant data can be distinguished from the non-redundant data in each channel and the effects of the non-redundant data or the noise in the data on the contamination level analysis can be substantially reduced.

In one exemplary embodiment, the non-redundant data may then be used to obtain additional information. For example, the non-redundant data may be caused by wavelength dependent scattering. Thus scattering in turn, may be used to obtain the size distribution of the scattering particles. However, alternate information, desired by those of ordinary skill in the art, may be obtained in a similar manner.

To select spectra of mud filtrate 125 (FIG. 1) and the formation oil 127 (FIG. 1) to determine contamination levels in fluid samples based on the measured OD data, the example apparatus 400 is provided with a spectra selector 420. The spectra selector 420 is configured to operate in accordance with the operations described below in connection with block 630 of the flowchart of FIG. 6B. The spectra selector 420 may alternatively or additionally be configured to determine contamination levels in fluid samples based on other types of measurements such as, for example, NMR measurements, density measurements, resistivity measurements, capacitance measurements, etc. To determine contamination levels of fluid samples, the example apparatus 400 is provided with a contamination value generator 422. The contamination value generator 422 is configured to operate in accordance with the operations described below in connection with block 632 of the flowchart of FIG. 6B. To determine an uncertainty value (e.g., a confidence value, a quality check value, etc.) indicative of the statistical variation of the contamination levels caused by noise in OD data, the example apparatus 400 is provided with an uncertainty value generator 424. The uncertainty value generator 424 is configured to operate in accordance with the operations described below in connection with block 634 of the flowchart of FIG. 6B.

FIGS. 5, 6A, 6B, and 7 are flowcharts of example methods that can be used to determine contamination levels in fluid samples extracted from a formation of a reservoir well (e.g., the formation F of the wellbore 102 of FIG. 1). The example methods of FIGS. 5, 6A, 6B, and 7 may be implemented using software and/or hardware. In some example implementations, the flowcharts can be representative of example machine readable instructions and the example methods of the flowcharts may be implemented entirely or in part by executing the machine readable instructions. Although the example methods are described with reference to the flowcharts of FIGS. 5, 6A, 6B, and 7, persons of ordinary skill in the art will readily appreciate that other methods to determine contamination levels in fluid samples may additionally or alternatively be used. For example, the order of execution of the blocks depicted in the flowcharts of FIGS. 5, 6A, 6B, and 7 may be changed, and/or some of the blocks described may be rearranged, eliminated, or combined. The example methods described below may be performed during a drilling process using, for example, the drill string 128 of FIG. 1. Alternatively or additionally, the example methods can be performed during a formation evaluation process separate from a drilling process using, for example, the borehole tool 200 of FIG. 2.

Figure 5:
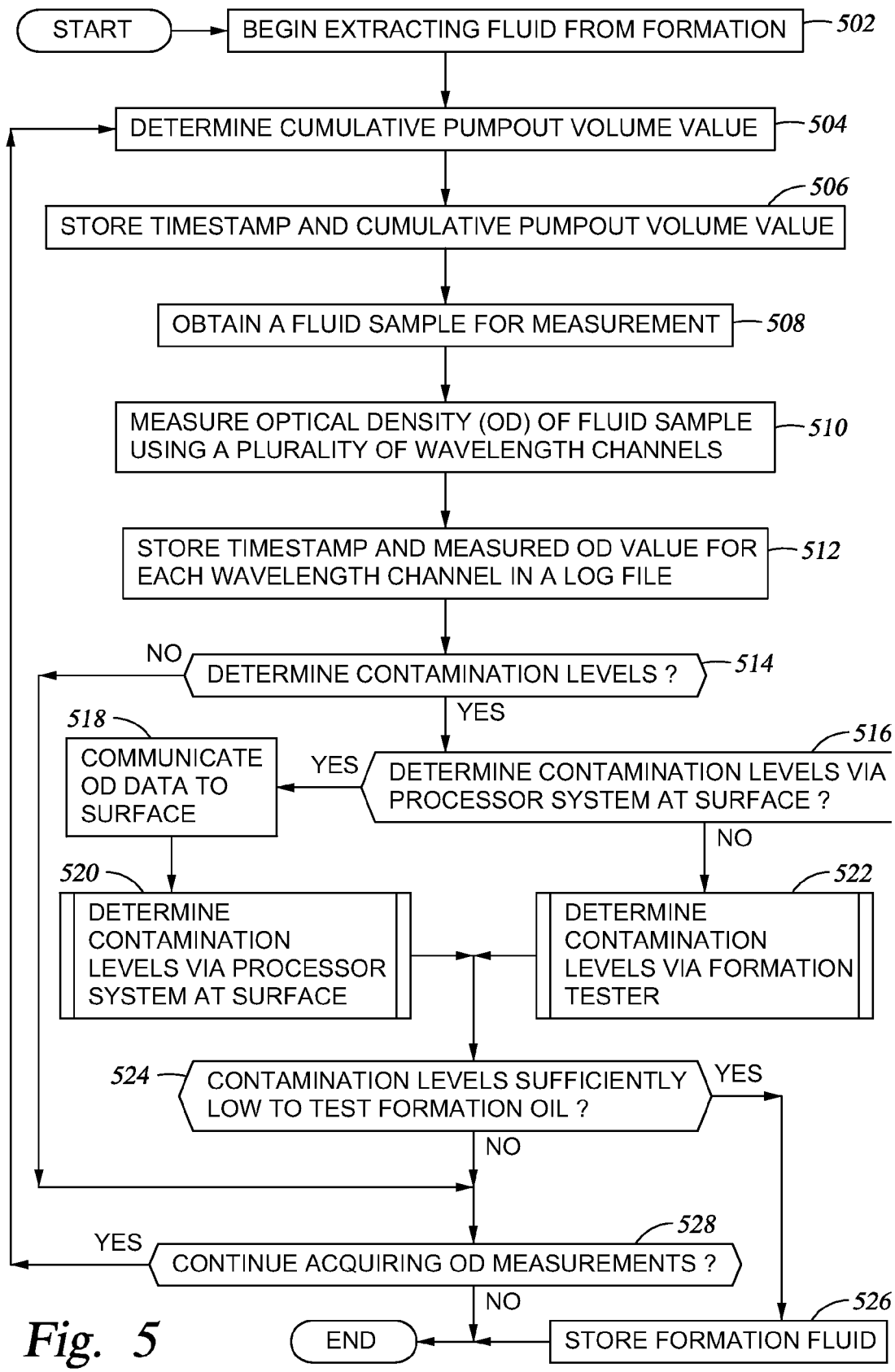
FIG. 5 depicts a flowchart of an example method that may be used to extract fluid samples from a formation and measure optical density properties of the formation fluid to implement the example methods and apparatus described herein.

Turning to FIG. 5, initially the port 304a of the probe 302a (FIG. 3A) begins extracting (or admitting) fluid from the formation F (block 502). In other example implementations both of the ports 304a-b can be configured to simultaneously extract fluid samples from the formation F. Initially, the extracted fluid typically contains a mixture of the oil 127 (FIG. 1) and the mud filtrate 125 (i.e., the contaminant) that permeates the formation F during a drilling process. After some time (e.g., minutes, hours, etc.) of pumping or extracting fluid from the formation F, the extracted fluid contains less of the mud filtrate 125 until the extracted fluid contains substantially little or none of the mud filtrate 125.

The controller 332 (FIG. 3A) determines a cumulative pumpout volume value (block 504) indicative of the cumulative volume of fluid that the formation tester 300 has extracted from the formation F since it initially started extracting fluid from the formation F. In an example implementation, the controller 332 can determine the cumulative pumpout volume value by periodically polling a volumetric flow rate sensor (not shown) in the flow path 326a and determining the cumulative volume value based on a plurality of volumetric flow rate values obtained over time. Alternatively, the cumulative pumpout volume value may be determined in any other manner. The controller 332 stores the cumulative pumpout volume value and a timestamp indicative of the time the controller 332 determined the cumulative pumpout volume value in a volume log file in the flash memory 336 (FIG. 3A) (block 506).

The spectrometer 324 (FIG. 3A) obtains formation fluid for measurement (block 508). For example, as discussed above in connection with FIGS. 3A and 3B, the spectrometer 324 is mounted in line with a flow line connected to an inlet port to draw formation fluid. The spectrometer 324 may be configured to measure the fluid extracted by the probe 302a (FIG. 3A) from the formation F (FIG. 1) at predetermined time-based intervals (e.g., every 5 minutes) or cumulative volume-based intervals (e.g., every 5,000 cubic centimeters of extracted fluid).

The spectrometer 324 then measures the optical density (OD) of the fluid sample using a plurality of wavelength channels (block 510). In the illustrated example, to determine contamination levels in the extracted fluid samples, the spectrometer 324 is configured to measure OD's of each sample using a plurality of channels (e.g., ten channels), each of which is set to a different wavelength of the light spectrum that can be selected from the range of visible to mid infrared light. At a particular wavelength ($\lambda$), the OD of a fluid sample typically will depend on the OD of the mud filtrate 125 at that wavelength (i.e., $OD_{\lambda,fil}$) and the OD of the formation oil 127 at that wavelength (i.e., $OD_{\lambda,oil}$). When selecting the wavelengths to be used to measure OD, wavelengths that are relatively more sensitive to contamination substances such as the mud filtrate 125 should be selected. A wavelength that measures OD of the mud filtrate 125 and the oil 127 to be substantially equal (e.g., $OD_{\lambda,fil}=OD_{\lambda,oil}$) should be avoided because such wavelengths have a relatively low sensitivity to the mud filtrate 125 relative to the formation oil 127. In addition, wavelengths that produce relatively noisy data because the fluid is almost opaque at those wavelengths should be avoided when the signal-to-noise (SNR) ratio is too low such that the noise level makes the data unusable. Accordingly, wavelengths having a relatively higher sensitivity to contamination substances such as the mud filtrate 125 may be selected to ensure that OD measurements can be used to distinguish between the mud filtrate 125 and the formation oil 127.

The controller 332 (FIG. 3A) then stores the measured OD value for each wavelength channel in an OD log file in the flash memory 336 (FIG. 3A) along with a timestamp indicative of the time the spectrometer 324 measured the OD values (block 512). The controller 332 then determines whether it is time to determine a contamination level (block 514). For example, in some example implementations, the controller 332 and/or the processor 146 (FIG. 1) at the surface may be configured to analyze the measured OD values at predetermined intervals (e.g., time-based intervals, cumulative pumpout volume-based intervals, intervals defined by the quantity of fluid samples measured after performing a previous measurement analysis, etc.) to determine the contamination levels in fluid samples.

If the controller 332 determines that it is time to determine the contamination levels of the measured fluid samples (block 514), the controller 332 or the processor 146 (FIG. 1) at the surface may then determine the contamination levels (block 516). For example, in some example implementations, the controller 332 may be configured to communicate the measured OD data from an OD log file in the flash memory 336 to the receiver subsystem 144 (FIG. 1) at the surface to enable the processor 146 to determine the contamination levels in the measured fluid samples. In other example implementations, the controller 332 may be configured to determine the contamination levels in the measured fluid samples while the formation tester 300 is in the wellbore 102.

If the processor 146 at the surface is to determine the contamination levels (block 516), the controller 332 communicates the measured OD data to the surface (block 518). For example, the controller 332 can communicate the measured OD data to the receiver subsystem 144 via the modem 340 (FIG. 3A). After the controller 332 communicates the measured OD data to the surface (block 518) the processor 146 determines the contamination levels (block 520) based on the received OD data. If the contamination levels are not to be determined at the surface (block 516), the controller 332 determines the contamination levels (block 522). An example process that can be used to determine the contamination levels in connection with blocks 520 and 522 is discussed below in connection with the flowcharts of FIGS. 6A and 6B. That is, the controller 332 can be configured to implement the example process of FIGS. 6A and 6B if the contamination levels are to be determined at the formation tester 300, and the processor 146 can be configured to implement the example process of FIGS. 6A and 6B if the contamination levels are to be determined at the surface.

After determining the contamination levels, the controller 332 (or the processor 146) determines whether the contamination levels in the most recently measured fluid samples are sufficiently low to test the formation oil 127 (FIG. 1) (block 524). For example, the controller 332 (or the processor 146) can be provided with a threshold value that defines the maximum contamination level allowable in a fluid sample. The threshold value can be used to select fluid samples to be measured for purposes of evaluating the quality of a formation. If the controller 332 (or the processor 146) determines that the contamination levels are sufficiently low to test the formation oil 127 (block 524), the formation tester 300 stores formation fluid (block 526) in the fluid store 330 of FIG. 3A. The selected fluid samples may then be analyzed for pressure, volume, and temperature.

If the controller 332 determines that contamination levels are not sufficiently low to test the formation oil 127 (block 524) or if the controller 332 determines that it is not time to determine the contamination levels of measured fluid samples (block 514), the controller 332 determines whether it should continue acquiring OD measurements (block 528). For example, the controller 332 may determine that it should continue to acquire OD measurements if, for example, it needs more OD measurements to perform a contamination level analysis. If the controller 332 determines that it should continue to acquire OD measurements, control is passed back to block 504. Alternatively, the controller 332 may determine that it should not continue to acquire OD measurements if, for example, no more OD measurements are required and the stored OD data is to be analyzed in a post process. If the controller 332 determines that it should not acquire any more OD measurements (block 528) or after the formation tester acquires test data for the formation oil 127 (block 526), the example process of FIG. 5 ends.

Figure 6A:
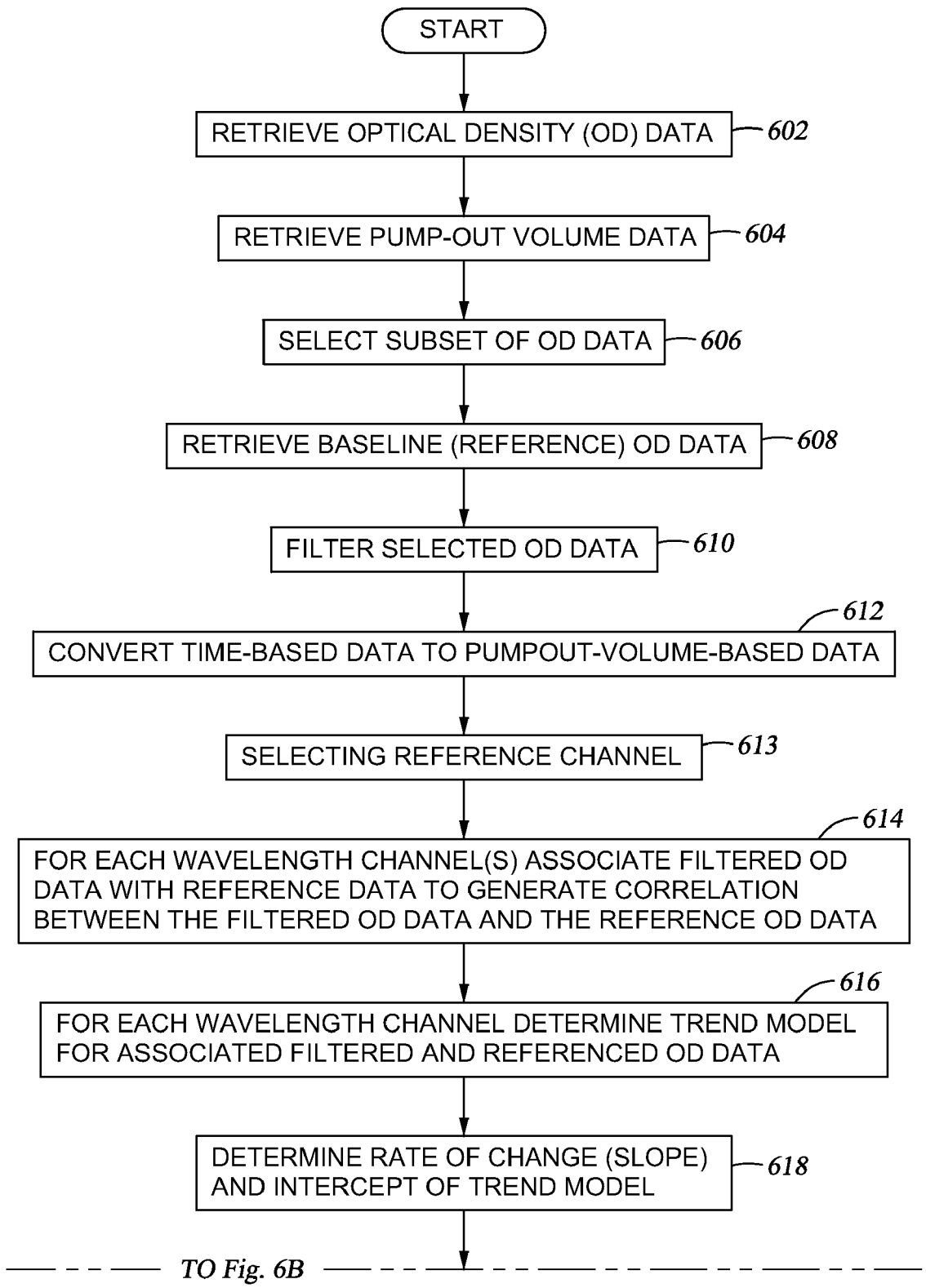
FIGS. 6A and 6B depict a flowchart of an example method that may be implemented in connection with the example method of FIG. 5 to determine the contamination levels of fluid samples extracted from a formation.
Figure 6B:
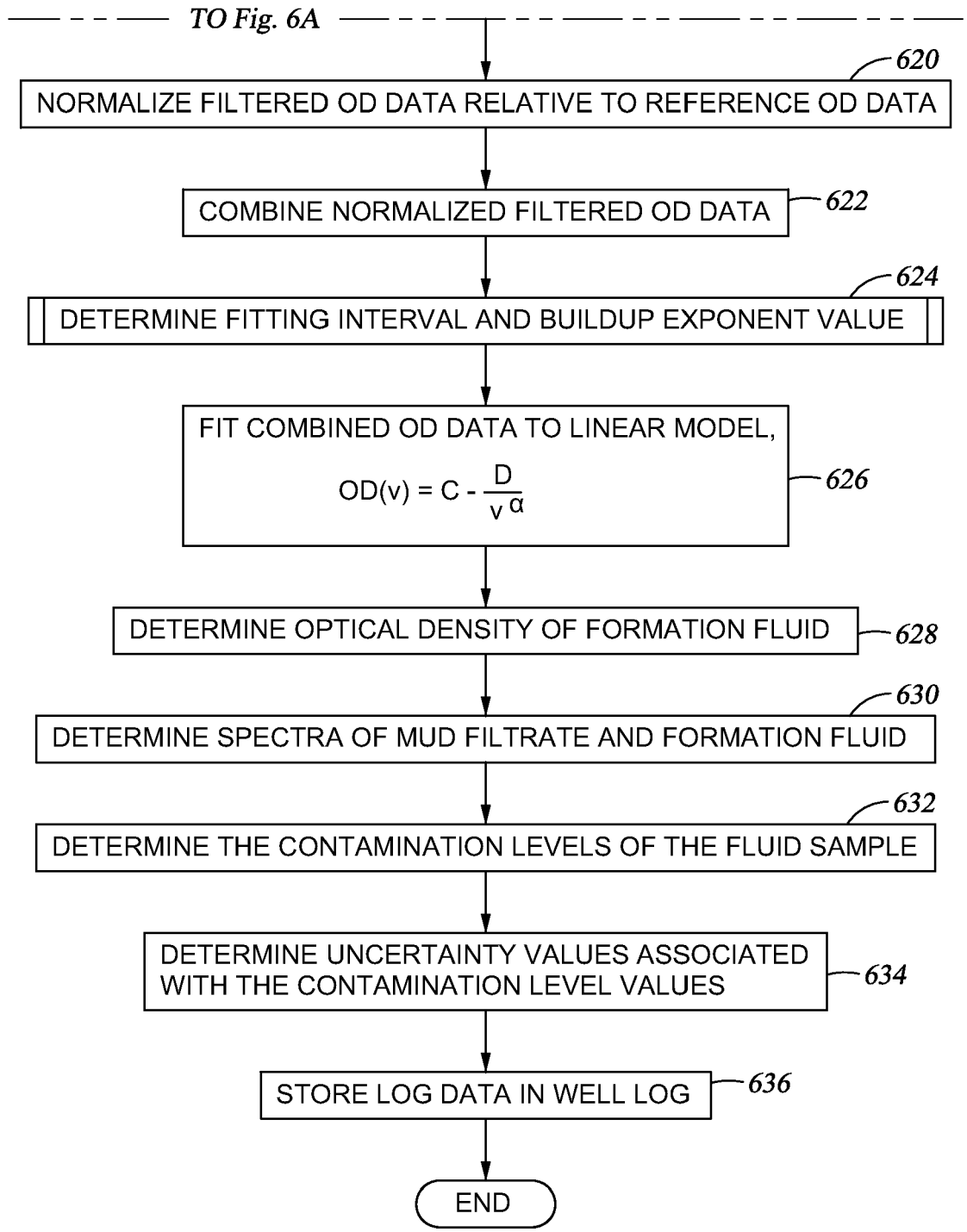

FIGS. 6A and 6B depict a flowchart of an example method that may be used to determine contamination levels in fluid samples extracted from the formation F (FIGS. 1 and 2) and to implement the operations of blocks 520 and 522 of FIG. 5. The example method of FIGS. 6A and 6B is described as being implemented using the example apparatus 400 of FIG. 4 and the example formation tester 300 (FIG. 3A). As discussed above the example apparatus 400 can be implemented using hardware, software, and/or a combination of hardware and software. In an example implementation, the flowchart of FIGS. 6A and 6B describes machine readable instructions that define the implementation of each of the blocks of the example apparatus 400. The machine readable instructions can be executed by the processor 146 (FIG. 1) at the surface and/or the controller 332 (FIG. 3A) while the formation tester 300 is in the wellbore 102 (FIG. 1).

As shown in FIG. 6A, initially, the data interface 402 (FIG. 4) retrieves the OD data (block 602) acquired using the plurality of wavelength channels at block 510 of FIG. 5. For example, the data interface 402 can retrieve the OD data from the flash memory 336 (FIG. 3A). The data interface 402 then retrieves the cumulative pumpout volume data (block 604) stored at block 506 of FIG. 5. For example, the data interface 402 can retrieve the cumulative pumpout volume data from the flash memory 336.

Figure 8:
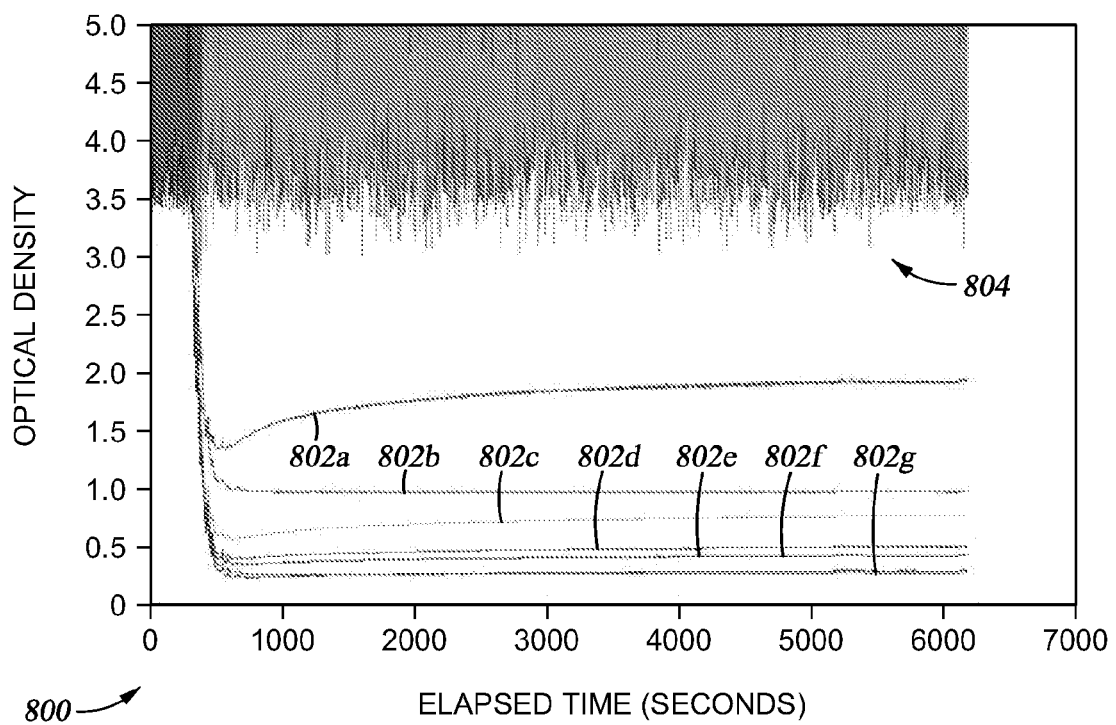
FIG. 8 illustrates a chart showing optical density data curve plots corresponding to various wavelength channels versus an elapsed time of fluid extraction from a formation.

The channel data selector 404 (FIG. 4) then selects a subset of the OD data (block 606) retrieved at block 602. More specifically, the channel data selector 404 selects OD data corresponding to the wavelength channels of the spectrometer 324 (FIG. 3A) that generated OD measurement values that facilitate determining contamination levels in the formation oil 127. In an example implementation, OD measurement values that facilitate determining the contamination levels are the OD measurement values that are within a particular OD range. For example, FIG. 8 illustrates a chart 800 showing OD data curve plots corresponding to various wavelength channels versus an elapsed time of fluid extraction. Each OD data curve plot represents OD data generated by a respective wavelength channel of the spectrometer 324 over approximately 6200 seconds. In the illustrated example of FIG. 8, the OD data curves that are useable for determining contamination levels are indicated by reference numerals 802a-802g, and the OD data curves that are not useable are generally indicated by reference numeral 804. The OD data generated using the baseline channel is indicated by reference numeral 802g.

In an example implementation, to select the subset of OD data at block 606 (FIG. 6A), the channel data selector 404 (FIG. 4) may be provided with an OD threshold value and a frequency of occurrence value. The threshold value defines a maximum OD value, and the frequency of occurrence value defines the maximum number of times during a period that OD data values corresponding to a particular channel wavelength can exceed the maximum OD value threshold before all of the OD data corresponding to that wavelength channel is disqualified for use in determining contamination levels. In the illustrated example of FIG. 8, the OD data of the wavelength channels corresponding to the curves 802a-g would be selected at block 606 with a threshold value equal to three optical density units (ODU). The frequency of occurrence value can be set based on, for example, the amount of noise that is acceptable in the OD data. For example, if the occurrence of a noise datum point every 1000 seconds is acceptable, the channel data selector 404 can be provided with a frequency of occurrence value equal to 0.001 Hz. Alternatively, the channel data selector 404 can be provided with a value (e.g., 100) equal to the number of acceptable noise datum occurrences in a test.

To select the subset of the OD data at block 606 (FIG. 6A), the comparator 406 can be configured to retrieve the OD threshold value and compare the threshold value to each OD value for each of the OD data curves 802a-g and 804. When the comparator 406 determines that an OD value exceeds the OD threshold value, the comparator 406 can communicate information to the channel data selector 404 indicating that an OD value exceeded the OD threshold value. The channel data selector 404 can then track the frequency of occurrence of OD values exceeding the OD threshold value for each wavelength channel. In this manner, the channel data selector 404 can select the OD data corresponding to wavelength channels that did not produce OD data or noise that exceeded the OD threshold value at a frequency greater than the frequency of occurrence. In this exemplary embodiment only an "upper" threshold is disclosed. However, a lower or combination of thresholds are also contemplated herein.

In the illustrated example of FIG. 8, the OD data curves 802a-g and 804 for all of the wavelength channels have OD data that exceeds the OD threshold value equal to three during approximately the first 500 seconds of measured fluid samples. Accordingly, in the illustrated example, the channel data selector 404 is configured to ignore the OD data acquired during the first 500 seconds.

Returning to FIG. 6A, the channel data selector 404 then retrieves baseline OD data values 802g generated using a designated baseline wavelength channel (block 608). The baseline OD data values 802g are generated by the spectrometer 324 (FIG. 3A) using a designated wavelength channel to quantify the effects of optical scatterings in all of the wavelength channels of the spectrometer 324 used to measure the fluid samples. Unlike optical absorption (that is measured using optical density) and which occurs when light enters a fluid sample and the fluid sample absorbs the light, optical scattering occurs when light enters a fluid sample and collides with or is obstructed by particles (e.g., sand particles or other debris), air bubbles, or emulsion (e.g., a mixture of oil and water causing a cloudy appearance), which causes the light to randomly scatter and not reach the optical detector. Optical scatterings may affect the measurements of some or all of the wavelength channels by causing noise or fluctuating OD data. In turn, the noise or erroneous OD data can affect the accuracy of the contamination levels determined based on the OD data. The effects of optical scattering in all of the wavelength channels is substantially the same regardless of wavelength. To substantially minimize or reduce the effects of optical scatterings, one of the wavelength channels of the spectrometer 324 is designated as a baseline channel that generates the baseline OD data 802g.

The filter 408 (FIG. 4) then filters the OD data for each wavelength channel selected at block 606 (block 610) to generate filtered OD data using the baseline OD data 802g selected at block 608. In the illustrated example, the filter 408 filters the OD data for each channel by subtracting the baseline OD data 802g from the OD data for each channel selected at block 606. By subtracting the baseline OD data 802g from the OD data corresponding to the other wavelength channels, the effects of optical scatterings are substantially reduced or eliminated from the OD data, thereby generating filtered OD data for each channel. In this manner, the filtered OD data can be used to determine substantially more accurate contamination levels than could otherwise be determined using OD data values affected by the optical scatterings.

Figure 9:
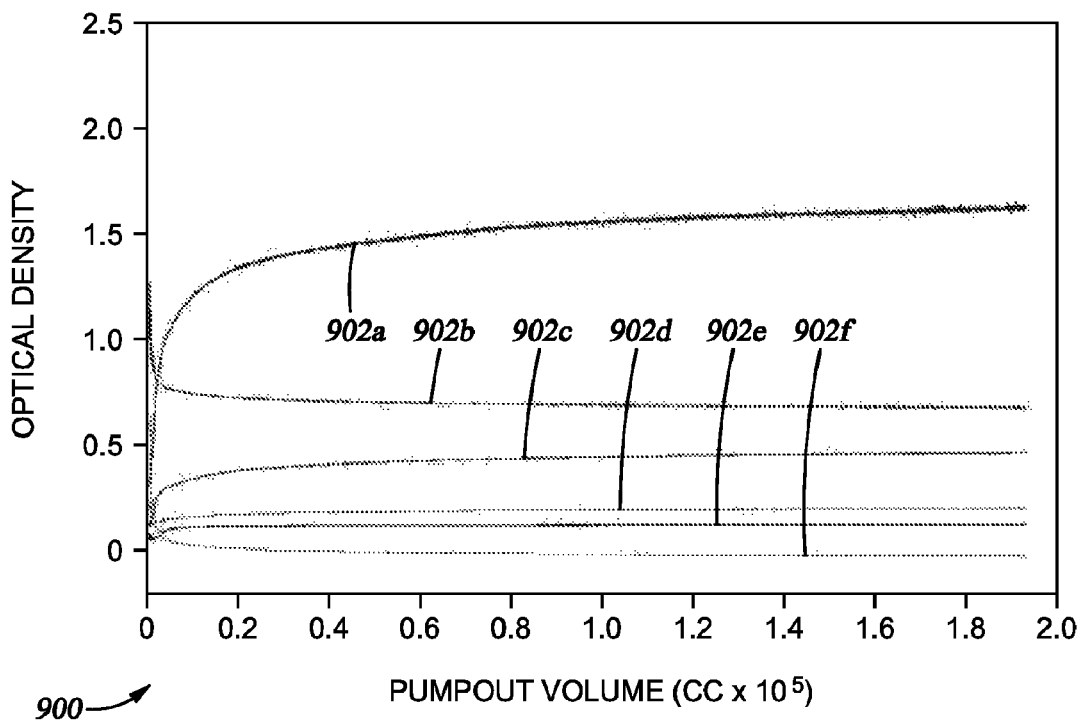
FIG. 9 illustrates an example chart showing curve plots corresponding to filtered optical density data versus a cumulative pumping volume for a plurality of wavelength channels.
Figure 10:
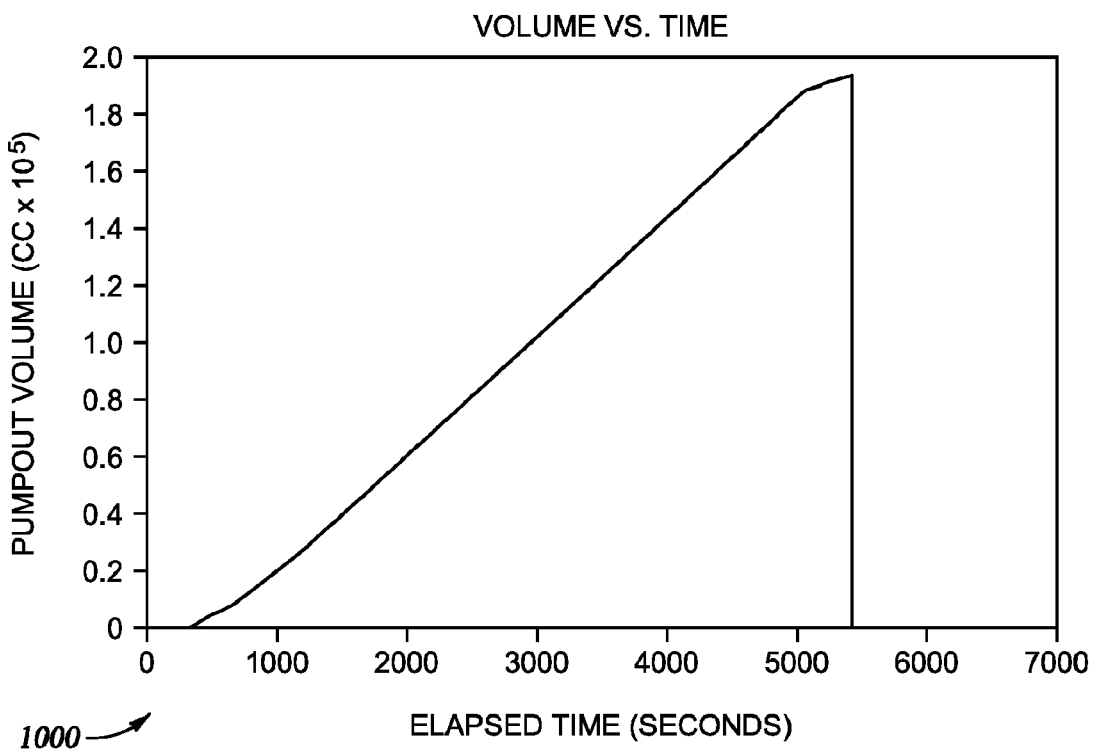
FIG. 10 illustrates a chart that shows a curve plot corresponding to a cumulative pumping volume of fluid extracted from a formation over a period of time.

The time-to-volume converter 410 (FIG. 4) then converts the filtered OD data from time-based data to pumpout-volume-based data (block 612). FIG. 9 illustrates an example chart 900 in which the filtered data are shown plotted for each channel as filtered OD data curves 902a-f as a function of pumpout volume. When the pumping rate or fluid extraction rate is not constant during the OD measurement process described above in connection with FIG. 5, volume-based data is relatively more suitable than time-based data for determining the buildup of oil concentration in the fluid samples relative to contamination levels. To facilitate processing the OD data, the time-based filtered OD data corresponding to each of the selected wavelength channels is converted to volume-based data. For example, the data interface 402 (FIG. 4) can access the flash memory 336 (FIG. 3A) to retrieve the cumulative pumpout volume data stored at block 506 (FIG. 5). As discussed above, the cumulative pumpout volume data is indicative of the cumulative volume of fluid that the formation tester 300 extracts from the formation F during an amount of time since it initially starts extracting fluid from the formation F. The cumulative pumpout volume data is stored in association with timestamps that correlate with timestamps stored in association with the measured OD data for each channel wavelength. An example volume versus time chart 1000 of FIG. 10 shows the cumulative pumpout volume data generated at block 506 of FIG. 5. In the illustrated example, the time-to-volume converter 410 uses the retrieved cumulative pumpout volume data to convert the filtered OD data generated at block 610 from time-based data to volume-based data using the timestamps associated with the cumulative pumpout volume data and the timestamps associated with the measured OD data (retrieved at block 602) used to determine the filtered OD data.

The filtered OD data for each channel ($OD_i(v)$) as a function of pumpout volume (v) is related to a contamination level ($\eta(v)$) as a function of pumout volume (v) as shown below in equation 4. In the illustrated example, one of the filtered OD data ($OD_i(v)$) having the largest dynamic range (e.g., the OD data 902a of FIG. 9) is selected as reference OD data ($OD_{ref}(v)$), as represented in block 613 of FIG. 6A. The reference OD data may, however, be selected by other criterions than the dynamic range. For example the reference OD data may be selected as the data corresponding to a wavelength channel where the filtrate has an optical density of zero, as will be discussed in greater detail below. The reference OD data ($OD_{ref}(v)$) as a function of pumpout volume (v) is related to the contamination level ($\eta(v)$) as a function of pumpout volume v as shown in equation 5 below.

$$OD_i(v)=\eta(v)\cdot OD_{i,fil}+(1-\eta(v))\cdot OD_{i,oil} \quad \text{Equation 4}$$

$$OD_{ref}(v)=\eta(v)\cdot OD_{ref,fil}+(1-\eta(v))\cdot OD_{ref,oil} \quad \text{Equation 5}$$

In equations 4 and 5 above, "ref" denotes the reference channel and "i" denotes the filtered channel at a particular wavelength, respectively. Each of the equations 4 and 5 above is substantially similar to equation 1 described above.

The data relationship processor 414 associates the reference OD data with the filtered OD data obtained from a plurality of wavelength channels to generate a correlation between the filtered OD data and the reference OD data (block 614). The filtered OD data values for the wavelength channels is associated with a cumulative pumpout volume value based on the time-to-volume conversion performed at block 612. In addition, the reference OD data values are also associated with a cumulative pumpout volume value. The data relationship processor 414 can be configured to associate the filtered OD data value with a corresponding reference OD data value based on respective matching or substantially matching cumulative pumpout volume values. Although not necessary, in some example implementations, the associated filtered OD data and reference OD data can be plotted on a chart for each wavelength channel to show the linear relationships between the associated data.

Figure 11A:
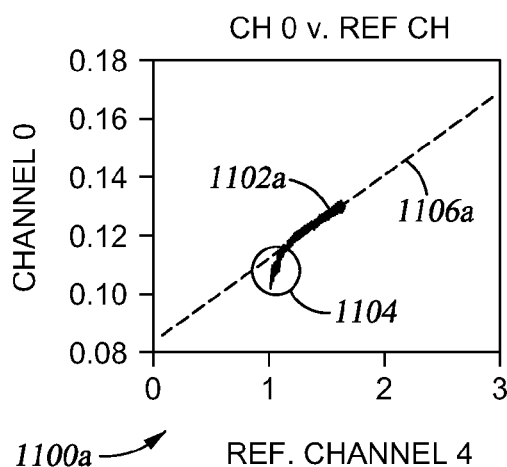
FIGS. 11A-11E illustrate charts showing cross plots of filtered optical density data associated with reference optical density data.
Figure 11B:
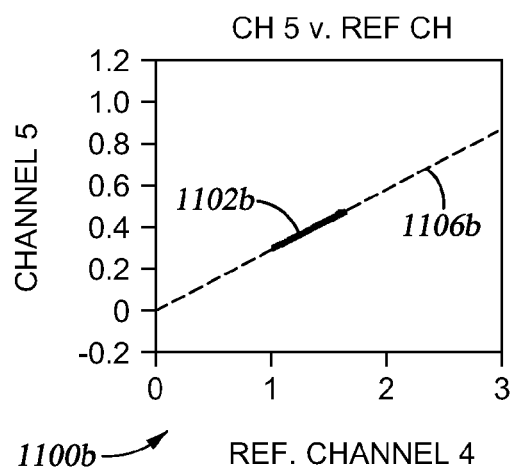
Figure 11C:
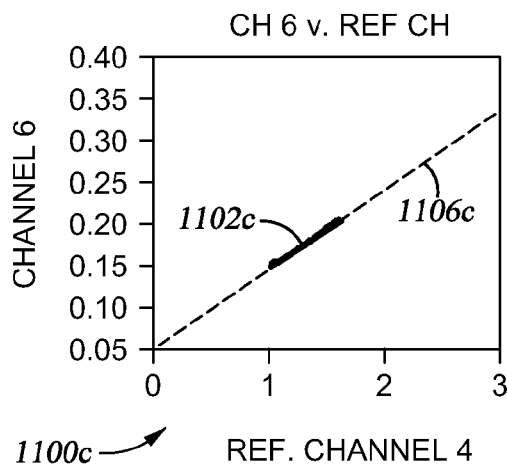
Figure 11D:
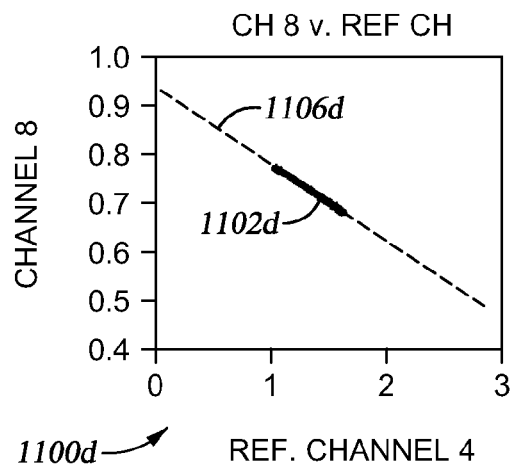
Figure 11E:
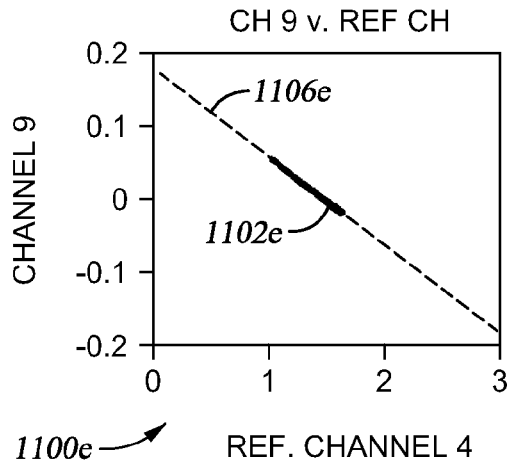

Turning briefly to FIGS. 11A-11E, charts 1100a-e show curve plots 1102a-e of correlations of the filtered OD data and reference OD data associated at block 614. The plotted curves of FIGS. 11A-11E are indicative of the linear relationships between the reference OD data and the filtered OD data corresponding to respective wavelength channels. Sometimes data acquired during an initial fluid extraction period is inaccurate because of, for example, formation cuttings, mud cake debris, etc. in the fluid samples. For example, the plotted curve 1102A of FIG. 11A shows data indicated by reference numeral 1104 that is inconsistent with the other plotted data. To substantially eliminate or reduce the effects of the erroneous data 1104, OD data collected during an initial period can be ignored or discarded for subsequent analysis.

Returning to block 616 of FIG. 6A, the data relationship processor 414 (FIG. 4) determines a trend model based on the correlations between the filtered and reference OD data associated at block 614. In an example implementation, the data relationship processor 414 can determine the trend models based on equations 4 and 5 above. In particular, for each wavelength channel i, the data relationship processor 414 can algebraically combine equations 4 and 5 above to determine the trend model of equation 6 below, which defines a linear relationship between the reference OD data $OD_{ref}(v)$ and the filtered OD data $OD_i(v)$.

$$OD_i(v)=A_i+B_i OD_{ref}(v) \quad \text{Equation 6}$$

The trend model of equation 6 above describes a straight line function having a slope value or rate of change value ($B_i$) representative of an amount of change in the filtered OD data $OD_i(v)$ relative to an amount of change the reference OD data $OD_{ref}(v)$. The trend model of equation 6 also has an intercept value $A_i$ that is equal to an OD value of the filtered OD data $OD_i(v)$ corresponding to an OD value of the reference OD data $OD_{ref}(v)$ that is equal to zero. The rate of change value $B_i$ and the intercept value $A_i$ are constant values related to OD values as shown in equations 7 and 8 below.

$$A_i = \frac{OD_{i,fil}OD_{ref,oil} - OD_{i,oil}OD_{ref,fil}}{OD_{ref,oil} - OD_{ref,fil}} \quad \text{Equation 7}$$

$$B_i = \frac{OD_{i,oil} - OD_{i,fil}}{OD_{ref,oil} - OD_{ref,fil}} \quad \text{Equation 8}$$

The rate of change value $B_i$ and the intercept value $A_i$ are related to the filtered optical density at wavelength channel "i" of the mud filtrate 125 (FIG. 1) $OD_{i,fil}$, the filtered optical density at wavelength channel "i" of the formation oil 127 (FIG. 1) $OD_{i,oil}$, the reference optical density of the mud filtrate 125 $OD_{ref,fil}$, and the reference optical density of the formation oil 127 $OD_{ref,oil}$ as shown in equations 7 and 8.

When the filtered optical density of the mud filtrate 125 (FIG. 1) $OD_{i,fil}$, the filtered optical density of the formation oil 127 (FIG. 1) $OD_{i,oil}$, the reference optical density of the mud filtrate 125 $OD_{ref,fil}$, and the reference optical density of the formation oil 127 $OD_{ref,oil}$ are unknown, the data relationship processor 414 uses the trend model of equation 6 above to determine the rate of change value $B_i$ and the intercept value $A_i$ (block 618 of FIG. 6A) for the wavelength channels by fitting data defining a straight line to the associated filtered and reference OD data depicted in the curve plots 1102a-e of FIGS. 11A-11E. In particular, for the wavelength channels, the data relationship processor 414 generates a correlation between the filtered OD data associated with that wavelength channel and the reference OD data. The curve plots 1102a-e are graphical representations of the correlations between the filtered OD data associated with the channels and the reference OD data. Dashed straight lines 1106a-e are shown in FIGS. 11A-11E to represent the fitted straight-line data fitted to the correlations. To fit straight-line data to the correlations, the data relationship processor 414 uses a known L1-norm fitting technique and treats the reference OD data $OD_{ref}(v)$ and the filtered OD data $OD_i(v)$ of equation 6 above as the independent and dependent variables, respectively. The rate of change value $B_i$ and the intercept value $A_i$ are fitting parameters or fitting values that define the fitted straight-line data and that can be determined based on the fitted straight-line data using known techniques. For example, the data relationship processor 414 can be configured to use a known algebraic technique for determining rate of change value $B_i$ and the intercept value $A_i$.

Turning to FIG. 6B, the normalizer 416 then normalizes the filtered OD data relative to the reference OD data (block 620).

Figure 12:
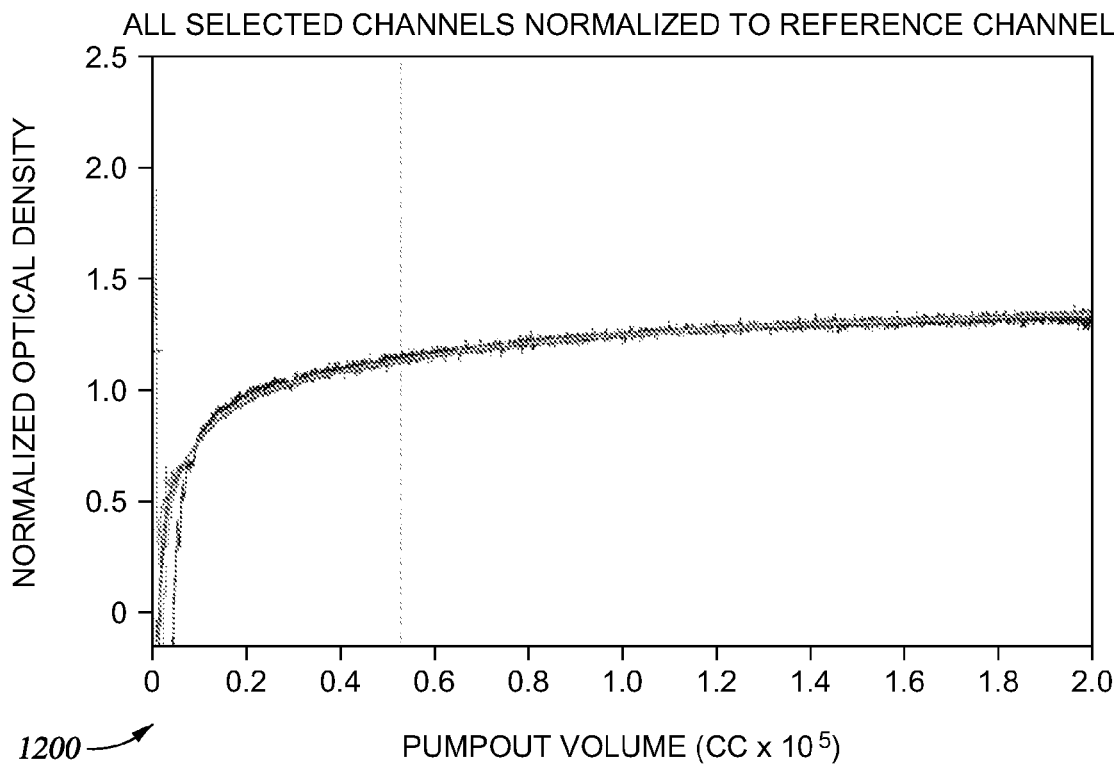
FIG. 12 illustrates a chart showing curve plots of normalized filtered optical density data for wavelength channels corresponding to the curve plots of FIG. 9.

FIG. 12 depicts a chart 1200 having curve plots of the normalized filtered OD data for the selected wavelength channels corresponding to the curve plots 902a-f depicted in FIG. 9. The normalizer 416 may be configured to normalize the filtered OD data to the reference OD data based on equation 9 below $$OD(v) = \frac{OD_i(v) - A_i}{B_i} \quad \text{Equation 9}$$

Equation 9 can be determined by algebraically rearranging equation 6 above. The normalizer 416 can use the rate of change value $B_i$ and the intercept value $A_i$ for each wavelength channel determined above at block 618 in connection with equation 9 to normalize the filtered OD data corresponding to each selected wavelength channel.

The data combiner 418 then combines the normalized OD data corresponding to all of the selected wavelength channels (block 622). For example, the data combiner 418 can be configured to combine normalized OD values corresponding to each selected wavelength channel and having matching or substantially matching volumes until all corresponding normalized OD values are combined to form combined OD data. In some example implementations, the data combiner 418 can be configured to combine the normalized OD data using an averaging process to average corresponding normalized OD values. Alternatively, the data combiner 418 can be configured to combine the normalized OD data using median or trimmed mean processes, which can be used to remove residual OD data corresponding to optical scatterings that remained in the normalized OD data after the filtering operation of block 610.

A trimmed mean is calculated by discarding a certain percentage of the lowest and the highest OD values and then determining an average of the remaining OD values. For example, a mean trimmed by 50% is computed by discarding OD values having magnitudes relatively 25% lower or higher than a mean OD value and determining an average of the remaining OD values. The median is the mean trimmed by 100%, and the average is the mean trimmed by 0%. A trimmed mean or median is relatively less susceptible than an average to the effects of noisy or inconsistent OD values corresponding to, for example, optical scatterings.

The example apparatus 400 determines a fitting interval or a fitting range (e.g., a straight-line fit range) and the buildup exponent value ($\alpha$) (block 624) based on the combined OD data. The example apparatus 400 can be configured to determine the fitting interval and the buildup exponent value ($\alpha$) using a derivative technique and/or a Bayesian Information Criterion (BIC) technique. In an example implementation in which the example apparatus 400 is configured to use the derivative technique, the example apparatus 400 is configured to determine the fitting interval by fitting straight-line data to data derived using the combined OD data in connection with equation 3 above $$\left(OD(v) = C - \frac{D}{v^\alpha}\right)$$

and then determining the buildup exponent value ($\alpha$) based on a slope of the fitted straight-line data.

Figure 7:
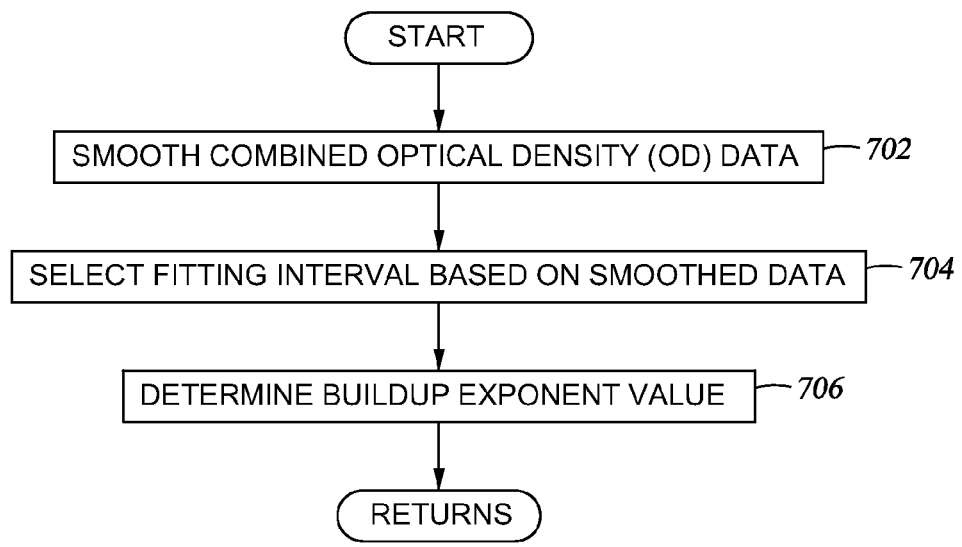
FIG. 7 depicts a flowchart of an example method that may be implemented in connection with the example method of FIGS. 6A and 6B to determine a fitting interval and a buildup exponent value to determine contamination levels in fluid samples extracted from a formation.

Turning briefly to FIG. 7, the flowchart of FIG. 7 depicts an example process that may be performed by the example apparatus 400 to implement the operation of block 624 using the derivative technique. Using the derivative technique, equation 3 is represented in natural logarithmic form as shown below in equation 10.

$$\ln\left(\frac{d(OD(v))}{d(\ln v)}\right) = \ln(\alpha D) - \alpha \ln v \quad \text{Equation 10}$$

Equation 10 depicts a linear model in which the logarithmic derivative of the combined OD data $$\left(\ln\left(\frac{d(OD(v))}{d(\ln v)}\right)\right)$$

is the dependent variable and a logarithmic volume (ln v) is the independent variable. Accordingly, equation 10 above indicates that the logarithmic derivative of the combined OD data $$\left(\ln\left(\frac{d(OD(v))}{d(\ln v)}\right)\right)$$

is linearly related to the logarithmic volume (ln v) and that the negative buildup exponent value ($-\alpha$) characterizes the slope (or rate of change) between the logarithmic derivative of the combined OD data $$\left(\ln\left(\frac{d(OD(v))}{d(\ln v)}\right)\right)$$

and the logarithmic volume (ln v).

To obtain the derivative of the combined OD data $$\left(\ln\left(\frac{d(OD(v))}{d(\ln v)}\right)\right)$$

of equation 10, the data fitter 412 (FIG. 4) performs a smoothing operation on the combined OD data (block 702) by fitting the combined OD data to the second-order polynomial model of equation 11 below using the known L1-norm fitting technique.

$$OD(v) = a + b(\ln v - \ln v_0) + c(\ln v - \ln v_0)^2, \text{ where}$$

$$\ln v_0 - \ln v_w/2 \leq \ln v \leq \ln v_0 + \ln v_w/2 \quad \text{Equation 11}$$

Figure 13:
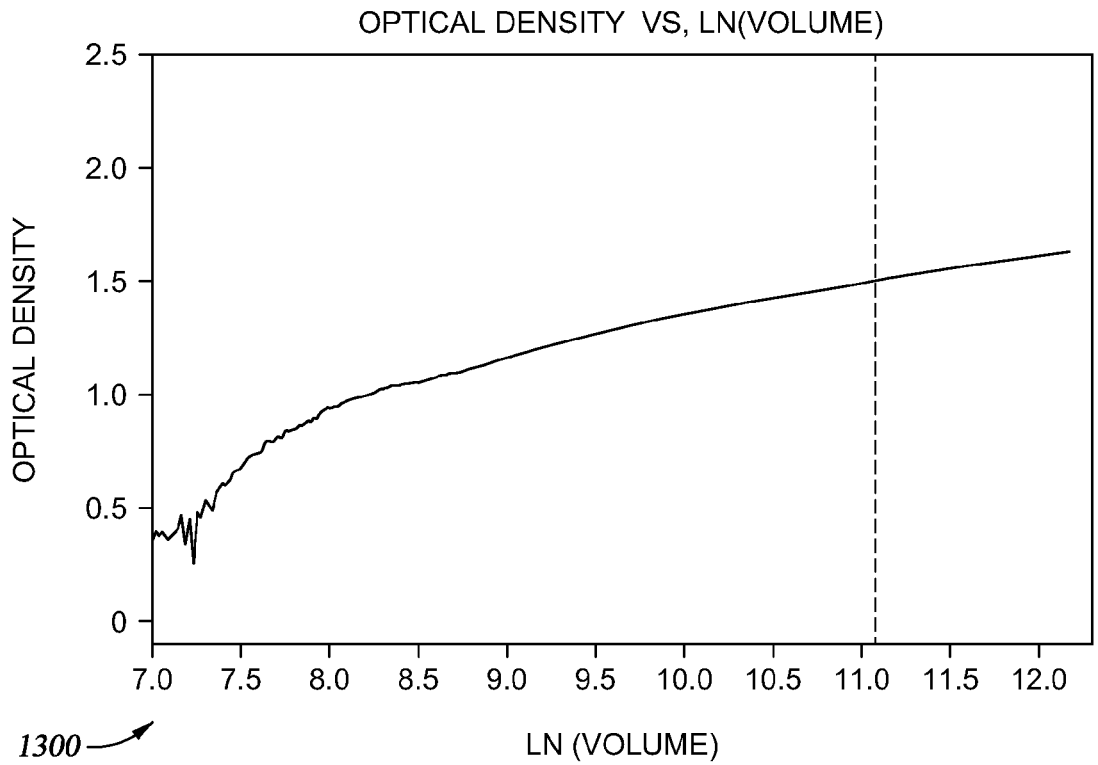
FIG. 13 illustrates a chart showing a curve plot corresponding to combined optical density data values versus logarithmic volume values.

In equation 11 above, a local window center parameter (ln $v_0$) and a local window size parameter (ln $v_w$) define a moving smoothing window used by the data fitter 412 to smooth the combined OD data relative to the logarithmic volume (ln v). A chart 1300 of FIG. 13 shows a curve plot of the combined OD data values versus the logarithmic volume (ln v). The data fitter 412 slides the smoothing window defined by the parameters ln $v_0$ and ln $v_w$ through each location specified by the logarithmic volume (ln v) values shown in FIG. 13. When the filter 408 finishes fitting the combined OD data to the second-order polynomial model of equation 11, the value (a) in equation 11 above represents the smoothed data at ln $v_0$, the value (b) in equation 11 represents the first-order derivative at ln $v_0$, and the value (c) represents the second-order derivative at ln $v_0$. With respect to equation 10, the derivative of the combined OD data $$\frac{d(OD(v))}{d(\ln v)}$$

is equal to the first-order derivative value (b)

$$\left(\text{i.e., } \frac{d(OD(v))}{d(\ln v)} = b \text{ at } \ln v_0\right).$$

Figure 14:
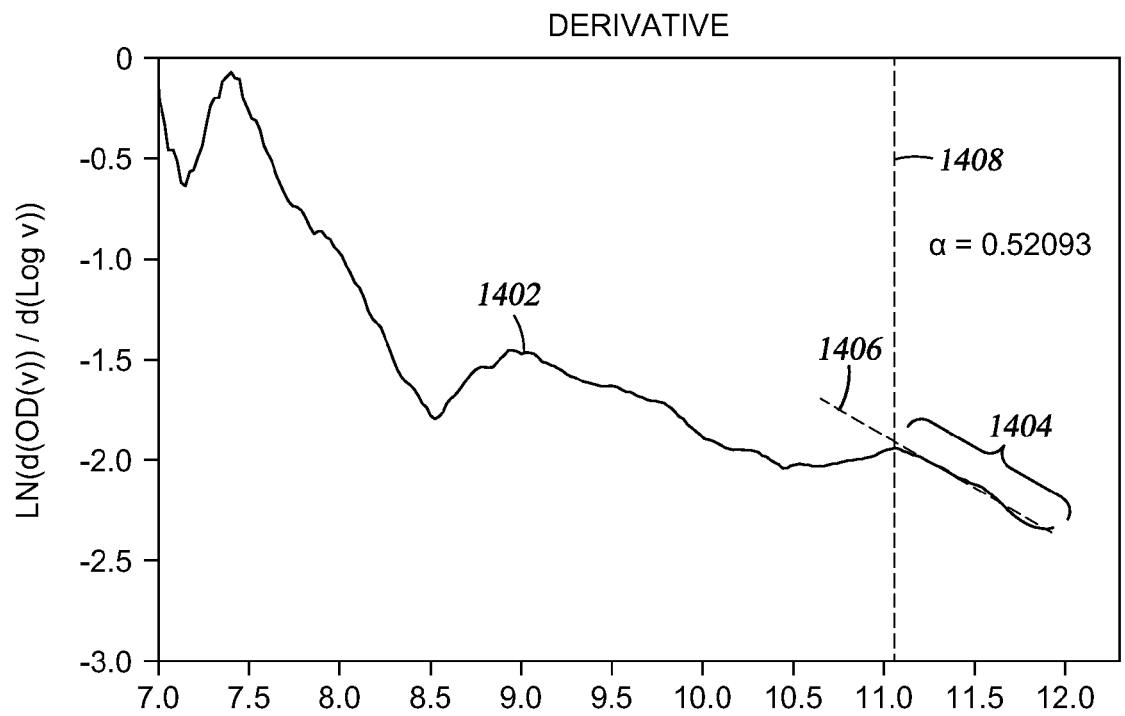
FIG. 14 depicts a chart showing a curve plot of logarithmic derivative smoothed data versus logarithmic volume values.

Returning to FIG. 7, the data fitter 412 then selects a fitting interval associated with the smoothed data (block 704). FIG. 14 depicts a chart 1400 having a plotted curve 1402 of the logarithmic derivative smoothed data generated by the data fitter 412. The chart 1400 shows that the smoothed data has no constant slope associated with the entire interval of the plotted curve 1402. However, a segment of the most recent data generally indicated by reference numeral 1404 is characterized by a constant slope. The data fitter 412 selects the segment of the most recent data 1404 as the fitting interval 1404 and fits straight-line data generally indicated by reference numeral 1406 to the fitting interval 1404. Although appearing short, the selected fitting interval 1404 displayed in logarithmic scale is actually about two-thirds of the entire plotted curve 1402. In the illustrated example of FIG. 14, a vertical line indicated by reference numeral 1408 indicates the beginning of the fitting interval 1404.

Returning to FIG. 7, the data relationship processor 414 then determines the buildup exponent value ($\alpha$) (block 706) based on the slope of the fitted straight-line data 1406 (FIG. 14). That is, the data relationship processor 414 determines the slope of the fitted straight-line data 1406 and sets the negative of the buildup exponent value ($-\alpha$) equal to the slope value. In the illustrated example, the data relationship processor 414 determines the slope value to be approximately −0.52, and thus the buildup exponent value ($\alpha$) to be approximately 0.52. After the data relationship processor 414 determines the buildup exponent value ($\alpha$), the example process of FIG. 7 returns control to the example process of FIGS. 6A and 6B.

Returning to FIG. 6B, in an alternative example implementation used to implement the operation of block 624, the example apparatus 400 can be configured to determine a fitting interval and the buildup exponent value ($\alpha$) based on the Bayesian Information Criterion (BIC) technique. The equation for implementing the BIC technique is shown equation 12 below.

$$BIC(\alpha, n, k) = \log\left(\frac{\sum_{i=0}^{n}(OD(v_i) - O\hat{D}(v_i, \alpha))^2}{n}\right) + k\frac{\log(n)}{n} \quad \text{Equation 12}$$

In equation 12 above, the value (n) defines the quantity of data points (e.g., combined OD data values) in the fitting interval, the value (k) is the quantity of unknown parameters (e.g., the parameters C, D, and $\alpha$ of equation 3 above are three unknown parameters) in the BIC model, and $O\hat{D}(v_i, \alpha)$ defines the best fit data for a given value of the buildup exponent ($\alpha$).

Figure 15:
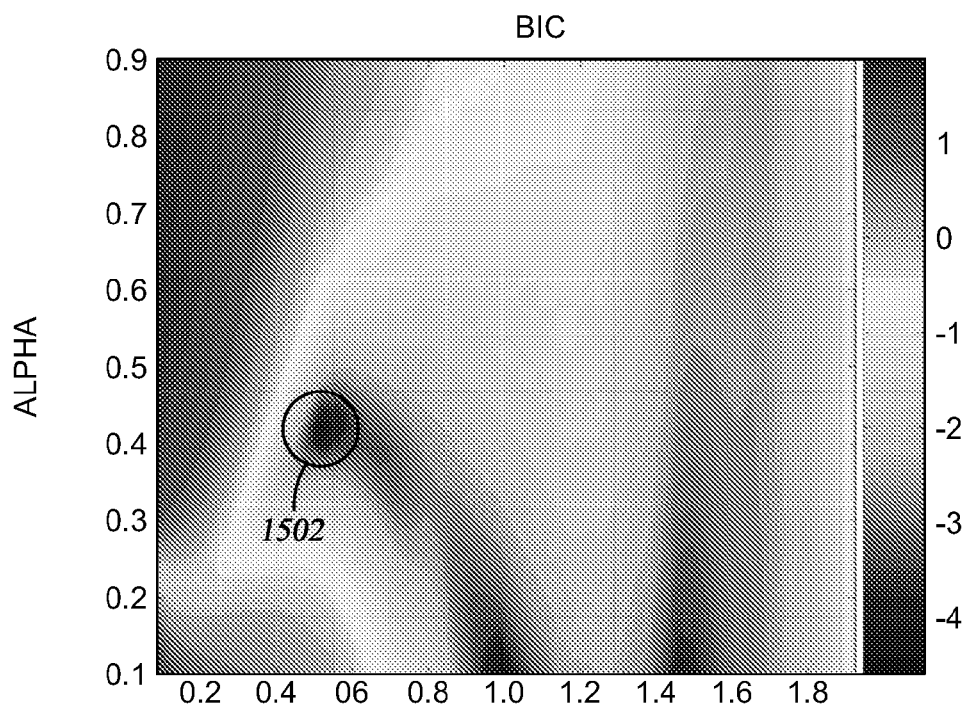
FIG. 15 depicts a chart showing a contour plot of a Bayesian Information Criterion model.

The parameters C, D, and $\alpha$ are unknown and, thus, the value (k) is equal to three. Setting the value (k) equal to three makes the BIC model of equation 12 a function of the value (n) and the buildup exponent ($\alpha$). The estimated values for the value (n) and the buildup exponent ($\alpha$) can be determined based on the minimum of BIC. In the illustrated example, the end of the fitting interval is marked as the last valid data point. Accordingly, when the value (n) is determined, the fitting interval can be selected based on the value (n). FIG. 15 shows a chart 1500 having a contour plot of the BIC with the horizontal axis labeled in terms of values that can be selected as the beginning of the fitting interval and the vertical axis as values that can be selected to be the buildup exponent ($\alpha$). In the illustrated example of FIG. 15, the minimum of the BIC is located at approximately the center of the circle marker 1502. The minimum of the BIC indicates a buildup exponent value ($\alpha$) of approximately 0.43 and a starting value of the fitting interval at approximately 51,000 cubic centimeters.

Although the example methods and apparatus are described as being configured to determine the fitting interval and the buildup exponent value ($\alpha$) using the derivative technique or the BIC technique, any other techniques may be used. For example, in some example implementations, the fitting interval and the buildup exponent value ($\alpha$) can be determined using an Akaike Information Criterion (AIC) technique.

Figure 16:
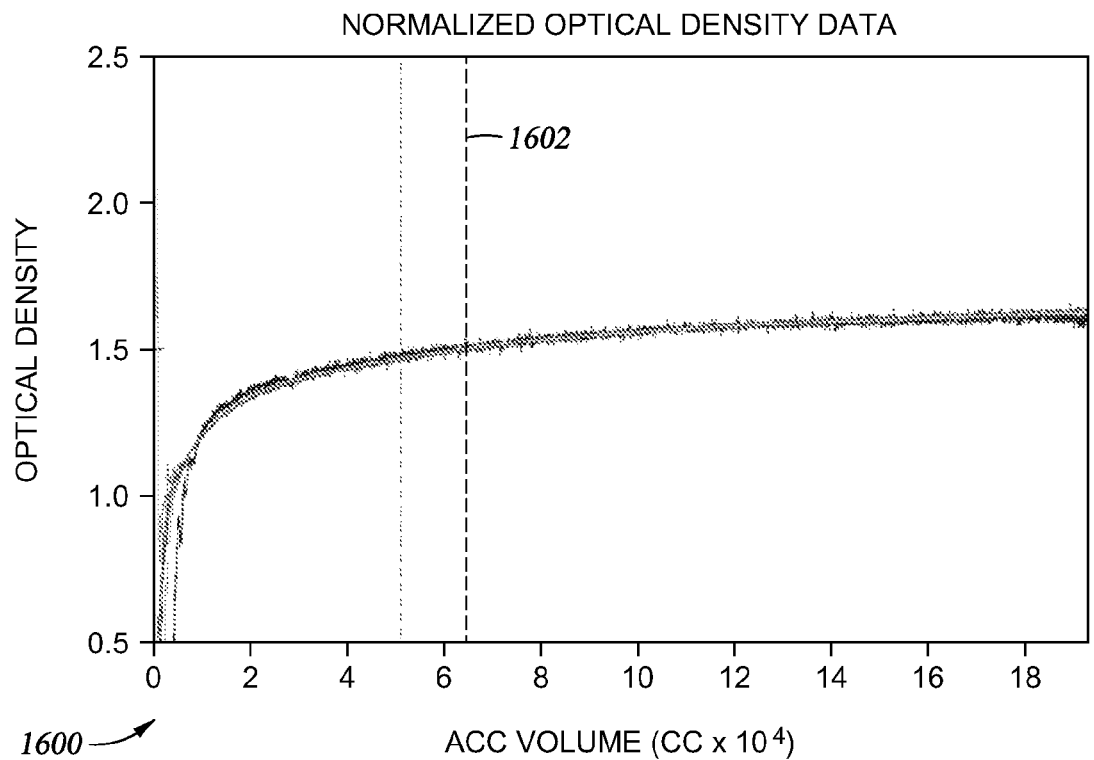
FIG. 16 depicts a chart showing normalized filtered optical density data for a plurality of wavelength channels.
Figure 17:
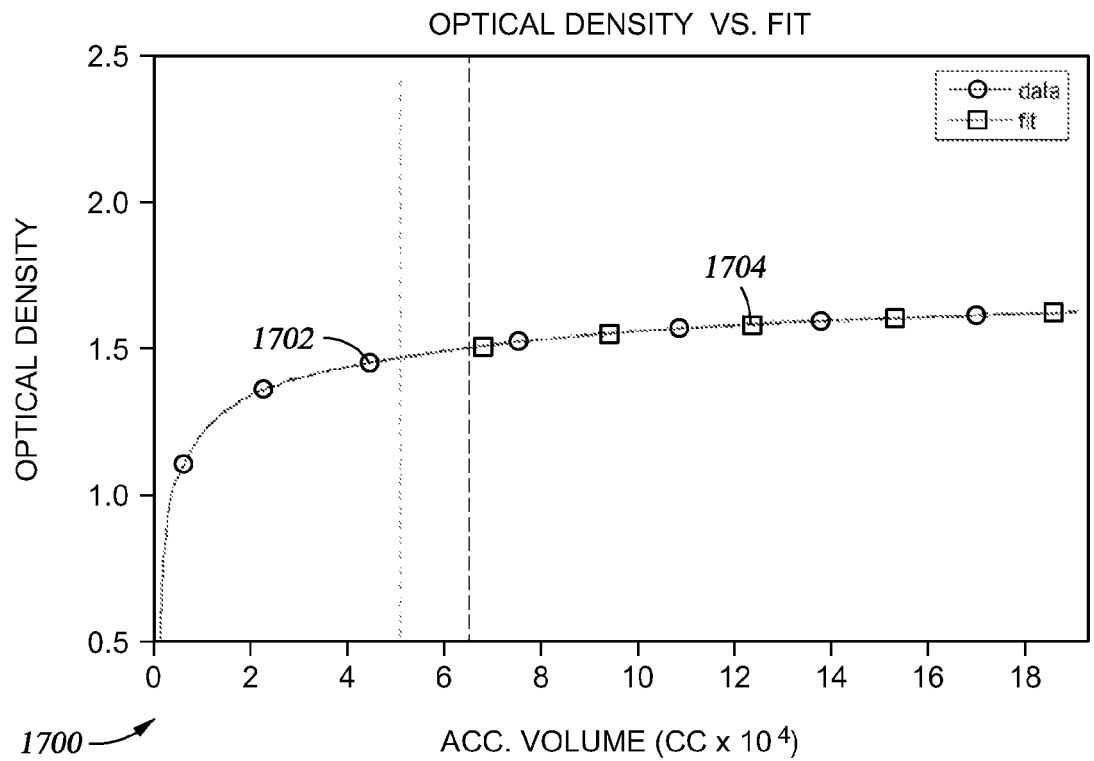
FIG. 17 depicts a chart showing a curve plot corresponding to combined optical density data and another curve plot corresponding to data fitted to the combined optical density data.

Returning again to FIG. 6B, the data fitter 412 fits the combined OD data determined at block 622 to the model of equation 3 above (block 626). FIG. 16 depicts a chart 1600 showing the normalized filtered OD data fitted using the linear model of equation 3 and a dashed line 1602 indicative of the beginning of the fitting interval 1406 (FIG. 14). FIG. 17 depicts a chart 1700 that shows a curve plot 1702 corresponding to the combined OD data determined at block 622 and another curve plot 1704 corresponding to fit data generated by the data fitter 412 to fit the combined OD data to the linear model of equation 3 over the fitting interval 1404 (FIG. 14).

Returning to FIG. 6B, the example apparatus 400 determines the OD of the formation oil 127 (FIG. 1) (block 628) based on the linear model of equation 3. To determine the OD of the formation oil 127 based on the combined OD data, the data relationship processor 414 determines the asymptotic optical density value C and parameter value D of equation 3 above based on the fitted data shown as the curve plot 1704 of FIG. 17. Because all of the fitted OD data was normalized to the reference OD data, the asymptotic optical density value C in equation 3 above for any wavelength channel is the OD of the formation oil 127 at the reference OD data for oil ($OD_{ref, oil}$).

Figure 18A:
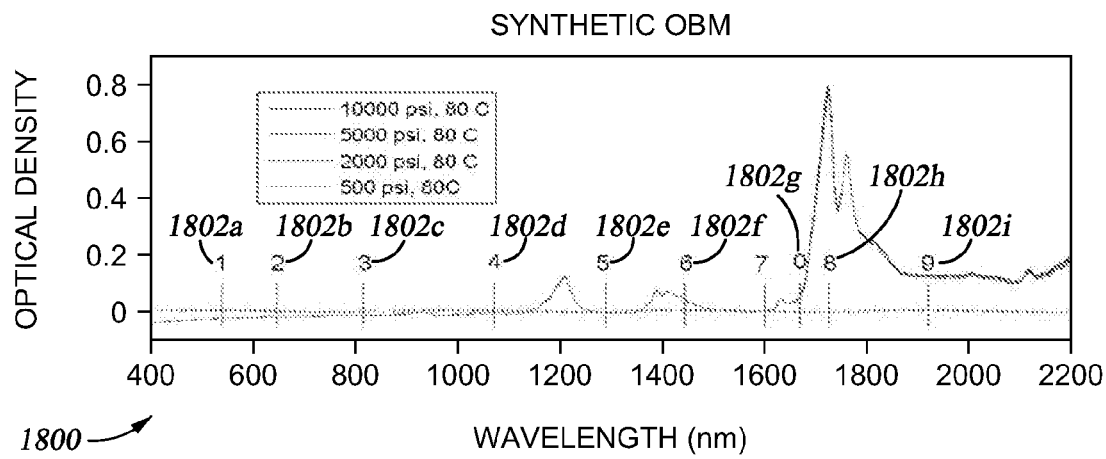
FIGS. 18A-18C depict charts that show curve plots of the wavelength spectra of three different types of oil-based mud filtrates.
Figure 18B:
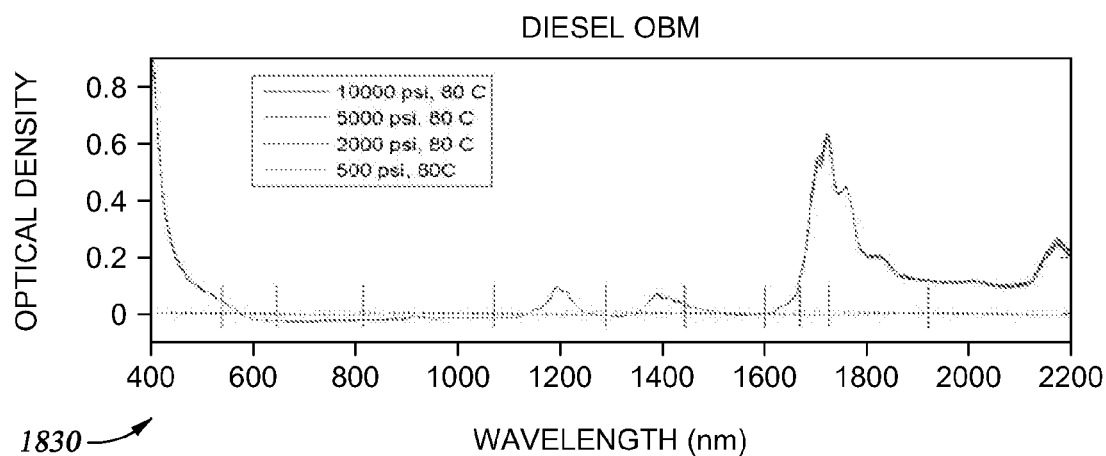
Figure 18C:
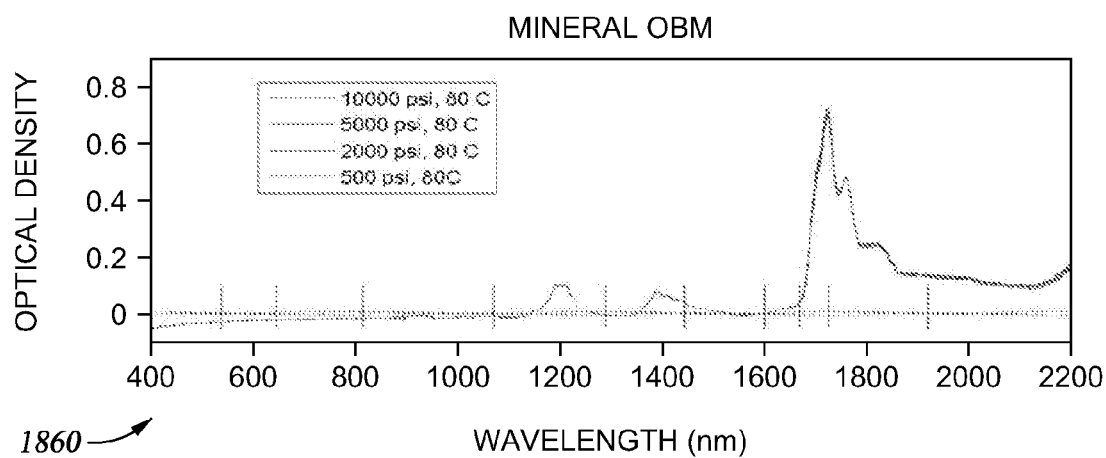

The spectra selector 420 then determines the spectra of the mud filtrate 125 (FIG. 1) and the formation oil 127 (FIG. 1) (block 630). The linear relationships determined for the OD data corresponding to all of the selected wavelength channels are valid regardless of the wavelength channel selected as the reference channel. However, selecting a particular wavelength channel as the reference channel facilitates determining the spectra of the mud filtrate 125 and the formation oil 127. FIGS. 18A-18C depict charts 1800, 1830, and 1860, each of which shows curve plots of the spectra of three different types of oil-based mud (OBM) filtrates at a temperature of 80° C. and various pressures. The plotted spectra have been normalized by subtracting the optical density at a baseline wavelength channel of 1600 nm. The tick markers 1802a-i on the charts 1800, 1830, and 1860 indicate the wavelengths of the various channels typically used in a formation tester spectrometer 324 to measure the optical densities of fluid samples.

Figure 19A:
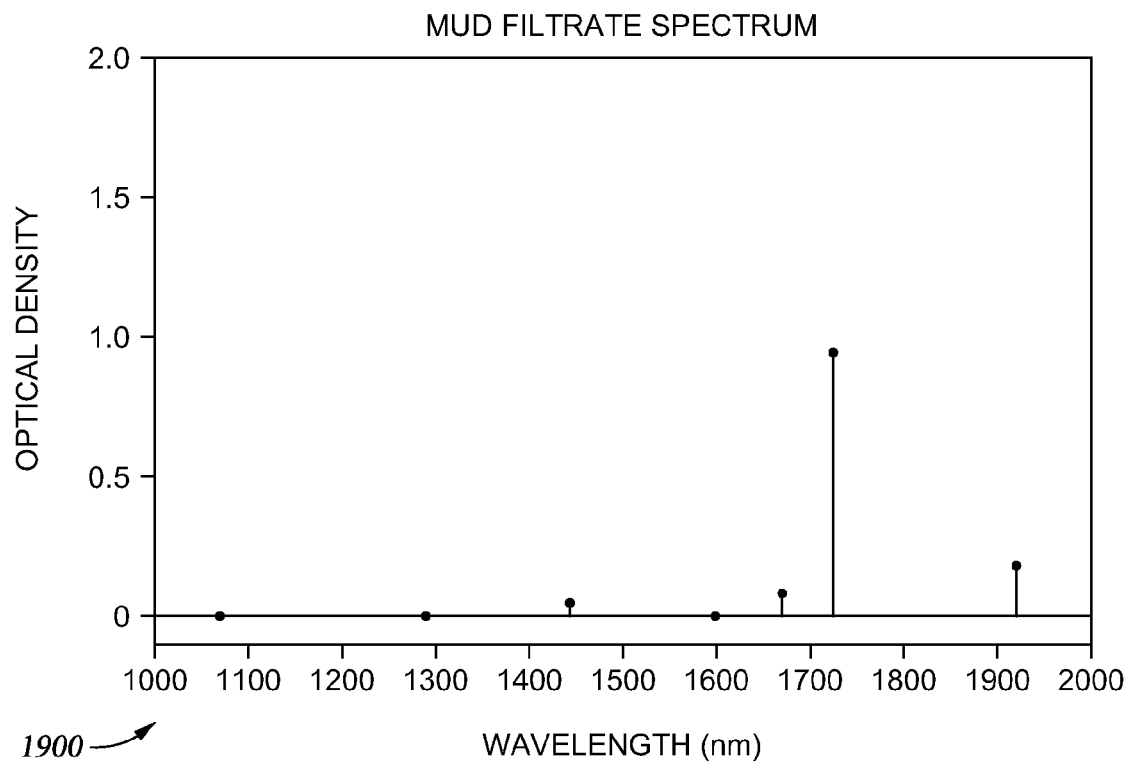
FIG. 19A depicts a chart showing a wavelength spectrum for a mud filtrate.
Figure 19B:
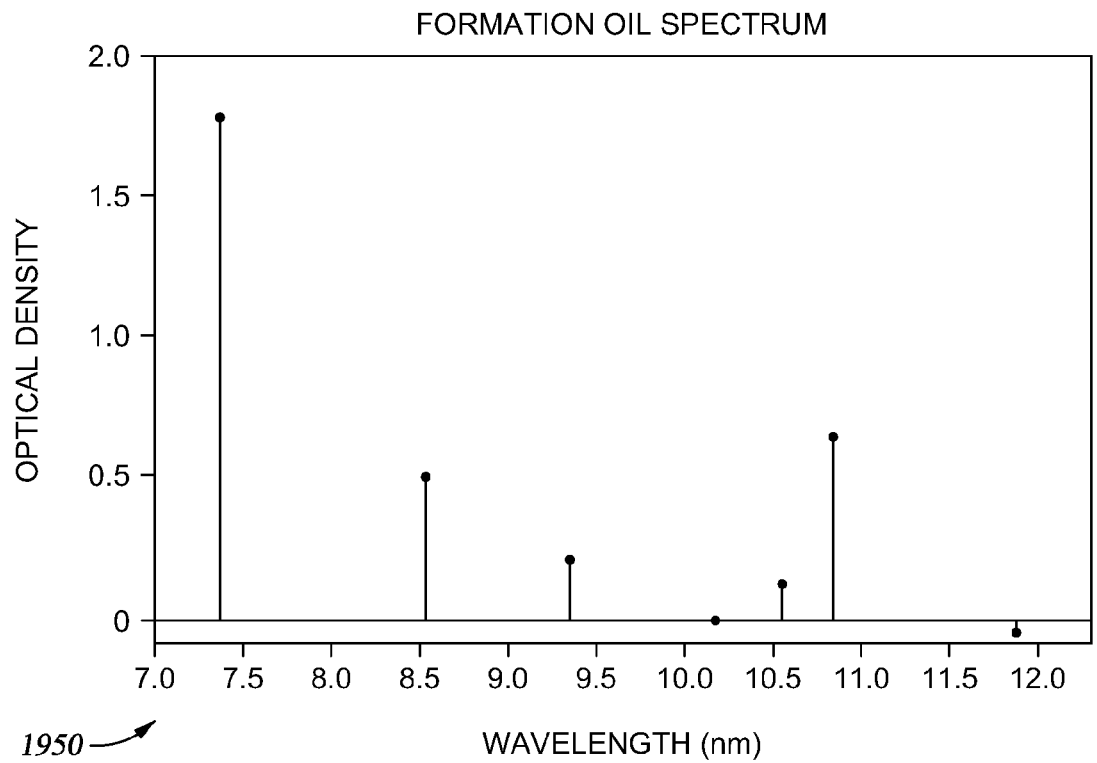
FIG. 19B depicts a chart showing a wavelength spectrum for a formation oil.

For the three different types of OBM filtrates, the OD values at the wavelength channels 4 and 5 are very close to zero (i.e., $OD_{ref,fil} \approx 0$). Selecting a channel having OD values close to zero as the reference channel facilitates determining the OD's of mud filtrate $OD_{t,fil}$ at the other channels. For example, referring to equation 7 above, by setting the value of $OD_{ref,fil}$ equal to zero, the optical density of filtrate $OD_{t,fil}$ at a particular channel is approximately equal to the intercept value $A_i$ of that channel. In this manner, the spectra selector 420 can determine the spectrum of the formation oil at all other channels (i.e., $OD_{i,oil}$) based on the rate of change value $B_i$ and the intercept value $A_i$ determined at block 618 and the reference OD data for oil ($OD_{ref,oil}$) determined at block 628. FIG. 19A depicts a chart 2000 showing the spectrum of the mud filtrate 125 (FIG. 1) and FIG. 19B depicts a chart 2050 showing the spectrum of the formation oil 127 (FIG. 1) determined by the spectra selector 420 at block 630 (FIG. 6B).

Similarly, it is possible to compute a property of the oil (e.g. its density). In one embodiment, raw or filtered mass density data are associated with reference optical density data at block 614. A trend model between the mass density data and the reference optical density data is determined at block 616. Because the mixing law is linear for both mass density and optical density, the trend model can also be expressed as an intercept and a slope at block 618. The reference optical density of the oil may be determined at block 626, utilizing only the reference optical density data as is well known in the art. Selecting a channel having OD value for the mud filtrate close to zero as the reference channel facilitates determining the mass densities of mud filtrate. In this case, the mass destiny of the mud filtrate is approximately equal to the intercept value determined at block 618. Further, the mass density of the oil may be determined from the intercept and the slope determined at block 618, and the reference OD of the oil determined at block 626.

Returning to FIG. 6B, the contamination value generator 422 (FIG. 4) then determines the contamination level values of the fluid samples (block 632). The contamination value generator 422 can determine the contamination level values using equation 2 above and the OD values of the filtrate and formation oil spectra determined at block 630. The contamination value generator 422 can be configured to determine a different contamination level value for each of the wavelength channels corresponding to the OD data selected at block 606. For example, in equation 2 above, the value $OD_\lambda$ is the measured OD at a particular wavelength channel, the optical density of mud filtrate $OD_{\lambda,fil}$ can be selected from the mud filtrate spectrum of FIG. 19A for the particular wavelength, and the optical density of formation oil $OD_{\lambda,oil}$ can be selected from the formation oil spectrum of FIG. 19B for the particular wavelength. The contamination value generator 422 then determines mean and standard deviation values ($\sigma$) of the contamination levels determined for each wavelength. The determined mean values are the contamination levels of the extracted fluid samples and the standard deviation values ($\sigma$) are related to the uncertainty of the contamination estimates.

Figure 20:
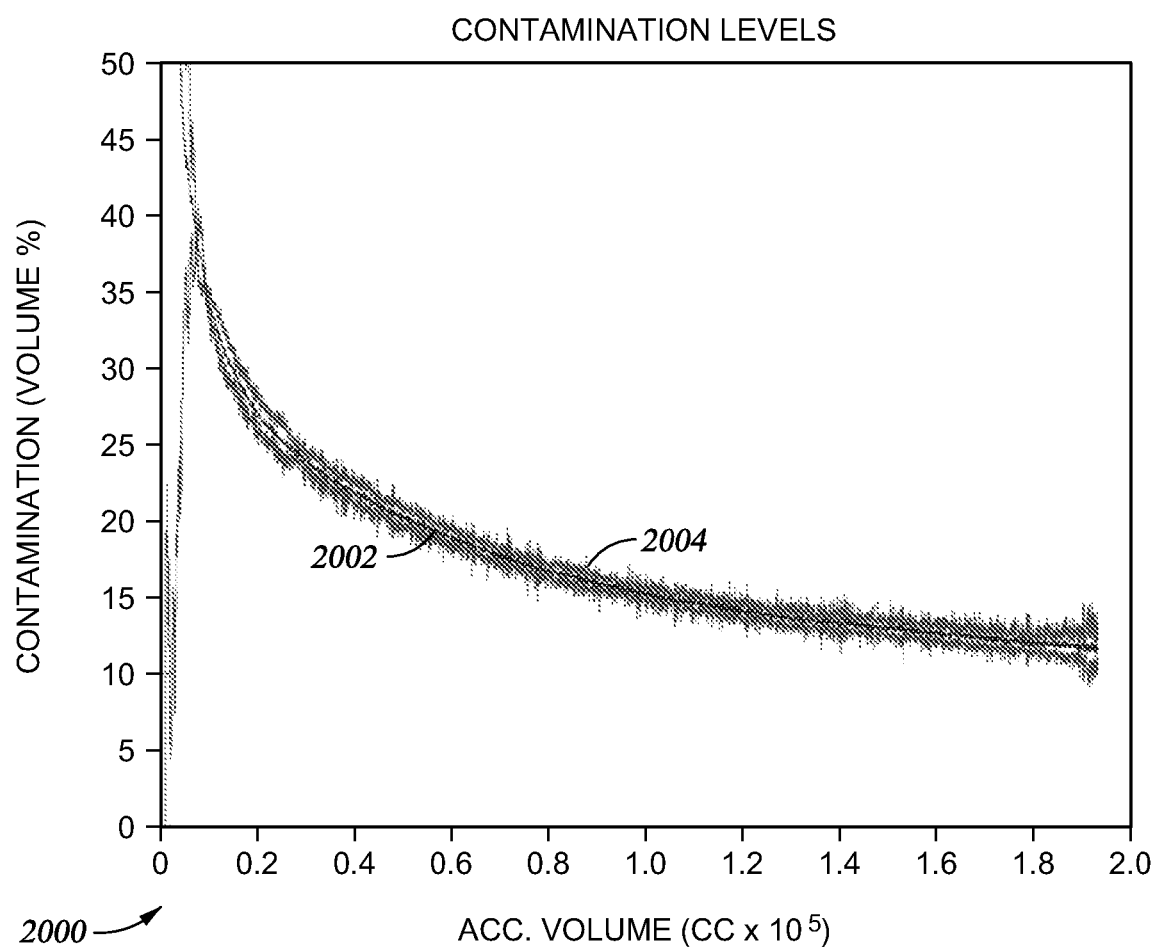
FIG. 20 depicts a chart having a curve plot corresponding to the contamination levels in fluid samples extracted from a formation and another curve plot corresponding to uncertainty values indicative of statistical variations of the contamination levels caused by noise in OD data.

The uncertainty value generator 424 then determines uncertainty values indicative of the accuracy of the contamination level values determined at block 632 (block 634). More specifically, the uncertainty value generator 424 determines the uncertainty values by subtracting twice the standard deviation ($2\sigma$) from the mean and adding twice the standard deviation ($2\sigma$) to the mean determined at block 632. FIG. 20 depicts a chart 2000 having a curve plot 2002 corresponding to the mean contamination levels determined at block 632 and a curve plot 2004 corresponding to the uncertainty values determined at block 634.

After the uncertainty value generator 424 determines the uncertainty values (block 634), the data interface 402 stores the log data (e.g., the contamination levels and the uncertainty values) determined at blocks 632 and 634 in a well log (block 636). The well log can be subsequently analyzed to determine the contamination levels in the measured formation fluid.

After the data interface 402 stores the log data in the well log (block 636), the example process of FIGS. 6A and 6B ends.

Although certain methods, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

What is claimed is:

1. A method of measuring fluid properties, comprising:
   operating a formation tester to obtain first property data indicative of a first fluid property of a formation fluid and second property data indicative of a second fluid property of the formation fluid, wherein the formation tester is configured to be positioned within a wellbore via a conveyance comprising one of drill-pipe, coiled tubing, wireline, and wired-drill-pipe, and wherein the wellbore extends into a formation comprising the formation fluid;
   generating a trend model based on an association between the first and second property data; and
   determining a parameter based on the trend model indicative of an amount of change of the first property data relative to an amount of change of the second property data.

2. The method of claim 1 wherein the first and second property data are indicative of an optical density property of the formation fluid at first and second wavelengths, respectively.

3. The method of claim 1 further comprising normalizing the first property data using the parameter.

4. The method of claim 1 further comprising measuring first and second fluid properties of the formation fluid a plurality of times to generate the first and second property data.

5. The method of claim 1 wherein the formation tester comprises:
   an inlet;
   a flow line fluidly connected to the inlet;
   a pump operatively coupled to the flow line to draw the formation fluid into the formation tester through the inlet;
   a first sensor coupled to the flow line to measure the first fluid property; and
   a second sensor coupled to the flow line to measure the second fluid property.

6. The method of claim 1 further comprising determining log data based on the parameter.

7. The method of claim 6 further comprising storing the log data in a well log.

8. The method of claim 6 wherein the formation fluid includes first and second fluid components, and wherein the log data is indicative of a characteristic of at least one of the first and second fluid components.

9. The method of claim 8 wherein the first fluid component is formation connate fluid and the second fluid component is drilling fluid filtrate.

10. The method of claim 6 wherein the log data comprises contamination level data.

11. The method of claim 10 further comprising determining uncertainty data indicative of an accuracy of the contamination level data.

12. The method of claim 1 further comprising measuring the first fluid property of the formation fluid at a plurality of points, wherein the points are obtained at least one of various times and various formation fluid volumes.

13. The method of claim 12 further comprising correlating the plurality of points of the first fluid property to at least one of the times and volumes, wherein correlating comprises determining the value of a build-up exponent.

14. The method of claim 13 wherein determining the value of the build-up exponent comprises:
   determining logarithmic derivative data of optical density measurement data;
   determining a linear relationship between the logarithmic derivative data and the volumes; and
   determining a rate of change value based on the linear relationship, wherein the rate of change value is representative of an amount of change in the logarithmic derivative data relative to an amount of change in the fluid pumpout volume data.

15. The method of claim 14 wherein the optical density measurement data is generated using a plurality of wavelengths.

16. The method of claim 14 further comprising determining a contamination level in the fluid based on the rate of change value.

17. The method of claim 16 further comprising determining an uncertainty value indicative of an accuracy of the contamination level.

18. A method, comprising:
   operating a formation tester to obtain first property data indicative of a first fluid property of a formation fluid and second property data indicative of a second fluid property of the formation fluid, wherein the formation tester has been positioned within a wellbore via a conveyance comprising one of drill-pipe, coiled tubing, wireline, and wired-drill-pipe, and wherein the wellbore extends into a formation comprising the formation fluid;
   generating a trend model based on an association between the first and second property data; and
   determining a parameter based on the trend model indicative of an amount of change of the first property data relative to an amount of change of the second property data.

19. A method, comprising:
   using a formation tester to measure first and second fluid properties of a formation fluid a plurality of times to generate first and second property data, respectively, wherein the formation tester has been positioned within a wellbore via a conveyance comprising one of drill-pipe, coiled tubing, wireline, and wired-drill-pipe, and wherein the wellbore extends into a formation comprising the formation fluid;
   generating a trend model based on an association between the first and second property data;
   determining a parameter based on the trend model indicative of an amount of change of the first property data relative to an amount of change of the second property data.

20. The method of claim 19 wherein the formation tester comprises a flow line fluidly connected to an inlet, a pump operatively coupled to the flow line to draw the formation fluid into the formation tester through the inlet, and first and second sensors each coupled to the flow line to measure the first and second fluid properties, respectively.

* * * * *